US 6,691,702 B2

(12) United States Patent  
Appel et al.

(10) Patent No.: US 6,691,702 B2
(45) Date of Patent: *Feb. 17, 2004

(54) PORTABLE OXYGEN CONCENTRATION SYSTEM AND METHOD OF USING THE SAME

(75) Inventors: William Scot Appel, San Diego, CA (US); David Phillip Winter, Encinitas, CA (US); Brian Kenneth Sward, San Diego, CA (US); Masato Sugano, Tokyo (JP); Edmund Salter, Oceanside, CA (US); James A. Bixby, La Jolla, CA (US)

(73) Assignees: SeQual Technologies, Inc., San Diego, CA (US); Teijin Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/134,868

(22) Filed: Apr. 29, 2002

(65) Prior Publication Data

US 2003/0005928 A1 Jan. 9, 2003

Related U.S. Application Data

(63) Continuation-in-part of application No. 09/632,099, filed on Aug. 3, 2000.

(51) Int. Cl.[7] ...................... A61M 15/00; A61M 16/00; A62B 7/08; A62B 21/00
(52) U.S. Cl. ........................... 128/202.26; 128/201.25; 128/205.11; 128/204.22
(58) Field of Search .................. 128/201.25, 205.11, 128/205.18, 204.17, 204.22, 204.21, 202.26, 205.12, 204.18, 204.23, 204.26; 251/283

(56) References Cited

U.S. PATENT DOCUMENTS 4,077,779 A  3/1978  Sircar 4,469,494 A  9/1984  Van Weenen (List continued on next page.)

FOREIGN PATENT DOCUMENTS

| DE | 197 07 097 A1 | 2/1997 |
| EP | 0 266 051 A1 | 9/1987 |
| EP | 0 757 919 A1 | 2/1997 |
| EP | 0 312 910 A1 | 10/1998 |
| EP | 0 875 277 A1 | 11/1998 |
| EP | 0 884 086 A2 | 12/1998 |
| EP | 0 884 088 A1 | 12/1998 |
| EP | 0 884 086 A3 | 1/1999 |
| EP | 1 044 714 A1 | 10/2000 |
| EP | 1 044 715 A1 | 10/2000 |
| GB | 2 164 568 A | 3/1986 |
| WO | WO 97/32692 | 9/1997 |

OTHER PUBLICATIONS

Patent Abstracts from Japan; vol. 2000; No. 02; 29 Feb. 29, 2000 and JP 11 319095A (Sumitomo Bakelite Co., Ltd.); Nov. 24, 1999; Abstract.

Primary Examiner—Weilun Lo
Assistant Examiner—Michael G. Mendoza
(74) Attorney, Agent, or Firm—Procopio, Cory, Hargreaves & Savitch, LLP

(57) ABSTRACT

A portable oxygen concentrator system adapted to be readily transported by a user includes a rechargeable energy source and a concentrator powered by the energy source. The concentrator converts ambient air into concentrated oxygen gas for the user and includes a plurality of adsorption beds and a rotary valve assembly. The rotary valve assembly is relatively rotatable with respect to the plurality of adsorption beds to provide valving action for selectively transferring fluids through the plurality of adsorption beds for converting ambient air into concentrated oxygen gas for the user. The ratio of adiabatic power to oxygen flow for the concentrator is in the range of 6.2 W/LPM to 23.0 W/LPM.

34 Claims, 17 Drawing Sheets

U.S. PATENT DOCUMENTS

| | | | |
|---|---|---|---|
| 4,477,264 A | | 10/1984 | Kratz et al. |
| 4,491,459 A | | 1/1985 | Pinkerton |
| 4,576,616 A | * | 3/1986 | Mottram et al. ............... 95/96 |
| 4,801,308 A | | 1/1989 | Keefer |
| 4,859,217 A | | 8/1989 | Chao |
| 4,925,464 A | | 5/1990 | Rabenau et al. |
| 4,968,329 A | | 11/1990 | Keefer |
| 4,971,609 A | | 11/1990 | Pawlos |
| 5,074,892 A | | 12/1991 | Leavitt |
| 5,112,367 A | | 5/1992 | Hill |
| 5,114,441 A | | 5/1992 | Kanner et al. |
| 5,268,021 A | * | 12/1993 | Hill et al. ...................... 95/98 |
| 5,366,541 A | * | 11/1994 | Hill et al. ..................... 96/124 |
| 5,413,625 A | | 5/1995 | Chao et al. |
| RE35,099 E | | 11/1995 | Hill |
| 5,593,478 A | * | 1/1997 | Hill et al. ..................... 96/111 |
| 5,626,151 A | | 5/1997 | Linden |
| 5,730,778 A | * | 3/1998 | Hill et al. ...................... 95/12 |
| 5,807,423 A | | 9/1998 | Lemcoff et al. |
| 5,814,130 A | | 9/1998 | Lemcoff et al. |
| 5,814,131 A | | 9/1998 | Lemcoff et al. |
| 5,820,656 A | | 10/1998 | Lemcoff et al. |
| 5,827,358 A | * | 10/1998 | Kulish et al. ................. 96/115 |
| 5,882,380 A | * | 3/1999 | Sircar ............................ 95/98 |
| 5,890,490 A | | 4/1999 | Aylsworth et al. |
| 5,891,217 A | | 4/1999 | Lemcoff et al. |
| 5,893,944 A | | 4/1999 | Dong |
| 5,912,422 A | | 6/1999 | Bomard et al. |
| 5,928,189 A | | 7/1999 | Phillips |
| 6,010,317 A | | 1/2000 | Maget |
| 6,010,555 A | | 1/2000 | Smolarek et al. |
| 6,051,050 A | | 4/2000 | Keefer et al. |
| 6,056,804 A | * | 5/2000 | Keefer et al. ................... 95/96 |
| 6,068,680 A | * | 5/2000 | Kulish et al. ................... 95/98 |
| 6,143,056 A | | 11/2000 | Smolarek et al. |
| 6,152,991 A | | 11/2000 | Ackley |
| 6,176,897 B1 | * | 1/2001 | Keefer ............................ 95/98 |
| 6,253,778 B1 | | 7/2001 | Smolarek et al. |
| 6,311,719 B1 | * | 11/2001 | Hill et al. ................... 137/312 |
| 6,346,139 B1 | | 2/2002 | Czabala |
| 6,395,065 B1 | * | 5/2002 | Murdoch et al. ............... 95/22 |
| 6,471,744 B1 | * | 10/2002 | Hill ............................... 95/19 |
| 6,514,319 B2 | * | 2/2003 | Keefer et al. ................. 95/101 |
| 6,521,562 B1 | * | 2/2003 | Clem et al. .................. 502/214 |
| 6,551,384 B1 | * | 4/2003 | Ackley et al. ................. 95/96 |
| 2001/0023640 A1 | | 9/2001 | Keefer |

\* cited by examiner

| PRODUCT FLOW RATE (slpm) | RE-COVERY (%) | PRODUCT PURITY (%) | FEED PRES-SURE (psig) | VAC-UUM PRES-SURE (psig) | FLOW RATE (slpm) | | ADIABATIC WORK (W)* | | |
|---|---|---|---|---|---|---|---|---|---|
| | | | | | COMP. | VAC-UUM | COMP. | VAC-UUM | TOTAL |
| 3.0 | 55.1 | 91.7 | 7.7 | -7.0 | 23.8 | 20.8 | 17.9 | 20.6 | 38.5 |
| 3.0 | 53.6 | 90.4 | 7.2 | -7.0 | 24.1 | 21.1 | 17.1 | 21.2 | 38.3 |
| 3.0 | 53.6 | 90.9 | 7.2 | -7.0 | 24.2 | 21.2 | 17.2 | 21.2 | 38.4 |
| 1.0 | 54.6 | 91.6 | 9.0 | -7.0 | 8.0 | 7.0 | 6.9 | 7.0 | 13.9 |
| 2.0 | 57.2 | 92.0 | 10.6 | -7.0 | 15.3 | 13.3 | 15.2 | 13.3 | 28.4 |
| 3.0 | 54.9 | 92.3 | 9.6 | -7.5 | 24.0 | 21.0 | 21.8 | 22.9 | 44.7 |
| 2.8 | 51.7 | 93.6 | 10.1 | -7.4 | 24.1 | 21.3 | 22.9 | 22.8 | 45.8 |
| 2.5 | 46.3 | 94.5 | 10.3 | -7.5 | 24.3 | 21.8 | 23.5 | 23.8 | 47.2 |
| 3.2 | 56.3 | 90.7 | 9.9 | -7.5 | 24.6 | 21.4 | 23.0 | 23.3 | 46.3 |
| 3.4 | 58.4 | 88.0 | 9.9 | -7.0 | 24.4 | 21.0 | 22.8 | 20.9 | 43.7 |
| 2.0 | 46.9 | 94.7 | 12.1 | -7.1 | 19.3 | 17.3 | 21.3 | 17.5 | 38.8 |
| 2.2 | 51.3 | 94.3 | 11.9 | -7.2 | 19.3 | 17.1 | 21.0 | 17.6 | 38.6 |
| 2.4 | 55.6 | 93.6 | 11.7 | -7.3 | 19.3 | 16.9 | 20.8 | 17.7 | 38.5 |
| 2.5 | 57.9 | 92.7 | 11.1 | -7.3 | 19.1 | 16.6 | 19.7 | 17.4 | 37.1 |
| 2.8 | 61.8 | 89.0 | 11.3 | -7.2 | 19.2 | 16.4 | 20.0 | 16.9 | 37.0 |
| 1.5 | 58.1 | 94.3 | 10.8 | -7.2 | 11.2 | 9.8 | 11.3 | 10.1 | 21.4 |
| 1.5 | 59.9 | 94.0 | 10.8 | -7.2 | 11.2 | 9.7 | 11.3 | 10.0 | 21.3 |
| 1.6 | 67.3 | 90.1 | 10.4 | -7.3 | 11.2 | 9.4 | 10.9 | 9.9 | 20.8 |
| 1.0 | 64.0 | 94.1 | 9.0 | -7.2 | 7.0 | 6.0 | 6.1 | 6.2 | 12.3 |
| 1.2 | 70.4 | 86.3 | 8.5 | -7.4 | 7.0 | 5.8 | 5.8 | 6.2 | 12.0 |
| 1.1 | 68.1 | 90.3 | 8.7 | -7.3 | 7.0 | 5.9 | 5.8 | 6.2 | 12.0 |
| 2.5 | 45.5 | 94.4 | 9.5 | -6.1 | 24.7 | 22.2 | 22.3 | 18.8 | 41.1 |
| 2.8 | 50.5 | 93.7 | 9.7 | -6.2 | 24.8 | 22.0 | 22.8 | 18.9 | 41.7 |
| 3.0 | 54.1 | 92.5 | 10.1 | -6.3 | 24.4 | 21.4 | 23.2 | 18.6 | 41.8 |
| 3.2 | 56.3 | 90.7 | 9.9 | -6.4 | 24.6 | 21.4 | 22.9 | 18.8 | 41.7 |
| 3.5 | 59.2 | 87.4 | 9.7 | -6.4 | 24.6 | 21.1 | 22.7 | 18.8 | 41.5 |
| 1.0 | 46.0 | 90.9 | 5.8 | -5.3 | 9.4 | 8.4 | 5.5 | 5.9 | 11.5 |
| 2.0 | 47.8 | 90.5 | 6.7 | -5.4 | 18.0 | 16.0 | 12.0 | 11.6 | 23.6 |
| 3.0 | 48.2 | 90.7 | 10.1 | -5.6 | 26.9 | 23.9 | 25.6 | 17.9 | 43.5 |
| 1.0 | 52.3 | 92.3 | 5.7 | -6.1 | 8.4 | 7.4 | 4.9 | 6.1 | 11.0 |
| 1.0 | 51.3 | 91.1 | 5.3 | -6.0 | 8.5 | 7.5 | 4.6 | 6.2 | 10.8 |
| 2.0 | 51.6 | 92.4 | 7.3 | -5.9 | 17.1 | 15.1 | 12.2 | 12.2 | 24.4 |
| 2.0 | 52.4 | 91.5 | 7.1 | -5.9 | 16.6 | 14.6 | 11.7 | 11.8 | 23.5 |
| 3.0 | 48.6 | 89.9 | 8.5 | -5.8 | 26.4 | 23.4 | 21.8 | 18.3 | 40.1 |
| 3.0 | 48.9 | 90.7 | 8.8 | -5.8 | 26.5 | 23.5 | 22.6 | 18.4 | 40.9 |

FIG. 11

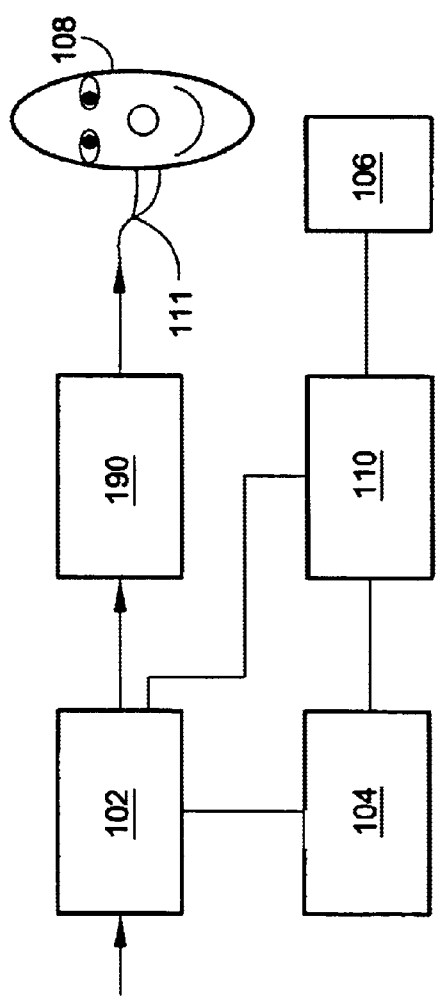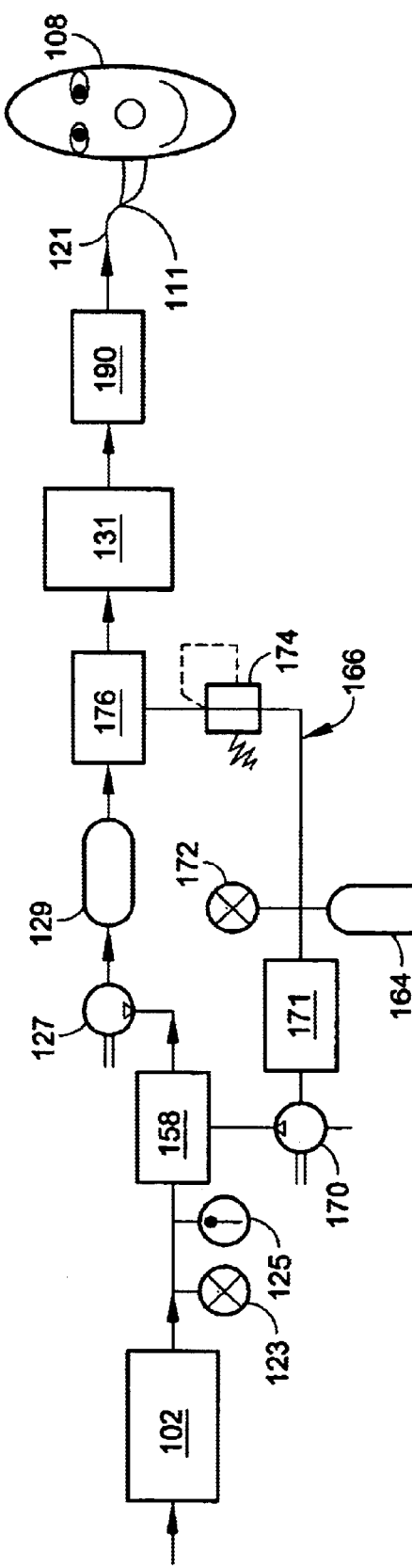

PORTABLE OXYGEN CONCENTRATION SYSTEM AND METHOD OF USING THE SAME

This application is a continuation-in-part of pending prior application Aer. No. 09/632,099, filed on Aug. 3, 2000.

BACKGROUND OF THE INVENTION

The field of this invention relates, in general, to oxygen concentrators and, in particular, to portable oxygen concentration systems for ambulatory respiratory patients that allow them to lead normal and productive lives.

There is a burgeoning need for home and ambulatory oxygen. Supplemental oxygen is necessary for patients suffering from lung disorders; for example, pulmonary fibrosis, sarcoidosis, or occupational lung disease. For such patients, oxygen therapy is an increasingly beneficial, life-giving development. While not a cure for lung disease, supplemental oxygen increases blood oxygenation, which reverses hypoxemia. This therapy prevents long-term effects of oxygen deficiency on organ systems—in particular, the heart, brain and kidneys.

Oxygen treatment is also prescribed for Chronic Obstructive Pulmonary Disease (COPD), which afflicts about six-hundred million people in the U.S., and for other ailments that weaken the respiratory system, such as heart disease and AIDS. Supplemental oxygen therapy is also prescribed for asthma and emphysema.

The normal prescription for COPD patients requires supplemental oxygen flow via nasal cannula or mask twenty four hours per day. The average patient prescription is two liters per minute of high concentration oxygen to increase the oxygen level of the total air inspired by the patient from the normal 21% to about 40%. While the average oxygen flow requirement is two liters per minute, the average oxygen concentrator has a capacity of four to six liters of oxygen per minute. This extra capacity is occasionally necessary for certain patients who have developed more severe problems, are not generally able to leave the home (as ambulatory patients) and do not require a portable oxygen supply.

There are currently three modalities for supplemental medical oxygen: high pressure gas cylinders, cryogenic liquid in vacuum insulated containers or thermos bottles commonly called "dewars," and oxygen concentrators. Some patients require in-home oxygen only while others require in-home as well as ambulatory oxygen depending on their prescription. All three modalities are used for in-home use, although oxygen concentrators are preferred because they do not require dewar refilling or exchange of empty cylinders with full ones. Home oxygen concentrators, however, do have their drawbacks. They consume relatively large amounts of electricity (350–400 Watts), are relatively large (about the size of a night stand), are relatively heavy (weight about 50 lbs.), emit quite a bit of heat, and are relatively noisy.

Only small high pressure gas bottles and small liquid dewars are truly portable enough to be used for ambulatory needs (outside the home). Either modality may be used for both in-home and ambulatory use or may be combined with an oxygen concentrator which would provide in-home use.

As described below, the current oxygen-supplying methods and devices have proven cumbersome and unwieldy and there has been a long-felt need for an improved portable device for supplying oxygen to the user.

For people who need to have oxygen and operate away from an oxygen-generating or oxygen-storage source such as a stationary oxygen system (or even a portable system which cannot be readily transported), the two most prescribed options generally available to patients are: (a) to carry with them small cylinders typically in a wheeled stroller; and (b) to carry portable containers typically on a shoulder sling. Both these gaseous oxygen and liquid oxygen options have substantial drawbacks, but from a medical view, both have the ability to increase the productive life of a patient.

The major drawback of the gaseous oxygen option is that the small cylinders of gaseous oxygen can only provide gas for a short duration. Another drawback is that a patient's high-pressure gaseous oxygen cylinders are not allowed in some locations such as airplanes because of safety considerations. A further drawback of the gaseous oxygen option is the refill requirement for oxygen once the oxygen has been depleted from the cylinder. These small gas cylinders must be picked up and refilled by the home care provider at a specialized facility. This requires regular visits to a patient's home by a provider and a substantial investment in small cylinders by the provider because so many are left at the patient's home and refilling facility. Although it is technically possible to refill these cylinders in the patient's home using a commercial oxygen concentrator that extracts oxygen from the air, this task would typically require an on-site oxygen compressor to boost the output pressure of the concentrator to a high level in order to fill the cylinders. Some disadvantages of common on-site oxygen compressors are that they are expensive, loud and emit a lot of heat. Additionally, attempting to compress the oxygen in pressurized canisters in the home is potentially dangerous, especially for untrained people.

This approach of course presents several safety concerns for in-home use. For example, in order to put enough of this gas in a portable container, it must typically be compressed to high pressure (~2000 psi) Compressing oxygen from 5 psi (the typical output of an oxygen concentrator) to 2000 psi will produce a large amount of heat. (Enough to raise the temperature 165 degrees C. per stage based on three adiabatic compression stages with intercooling.) This heat, combined with the oxygen which becomes more reactive at higher pressures, sets up a potential combustion hazard in the compressor in the patient's home. Thus, operation of a high-pressure gas system in the patient's home is dangerous and not a practical solution.

The convenience and safety issues are not the only drawbacks of this compressed oxygen approach. Another drawback is that the compressors or pressure boosters needed are costly because they require special care and materials needed for high pressure oxygen compatibility.

Turning now to the liquid oxygen storage option, its main drawback is that it requires a base reservoir—a stationary reservoir base unit within the patient's home about the size of a standard beer keg—which may be refilled about once a week from an outside source. Liquid oxygen can then be transferred from the patient's base unit to a portable dewar, which can be used by the ambulatory patient. Also, with the liquid oxygen option, there is substantial waste, as a certain amount of oxygen is lost during the transfer to the portable containers and from evaporation. It is estimated that 20% of the entire contents of the base cylinder will be lost in the course of two weeks because of losses in transfer and normal evaporation. These units will typically boil dry over a period of 30 to 60 days even if no oxygen is withdrawn.

Home refilling systems that produce liquid oxygen and have the capability of refilling portable liquid oxygen dewars have been proposed. However, these devices require the user to perform the task of refilling bottles and add tens of dollars per month to the user's electric bill, which is not reimbursable.

There are other complications with these portable high-pressure cylinders and liquid dewars. Typically, supplemental oxygen is supplied to the patient by a home care provider, in exchange for which the provider receives a fixed monetary payment from insurance companies or Medicare regardless of the modality. Oxygen concentrators are preferred by the provider as the least expensive option for supplying the patient's at-home needs. For outside the home use, however, only small high-pressure gas bottles and small liquid dewars are portable enough to be used for ambulatory needs. Either one of these two modalities may be used for both in-home and ambulatory use or may be combined with an oxygen concentrator, which would provide in-home use. In either case, the home care provider must make costly weekly or biweekly trips to the patient's home to replenish the oxygen. One of the objects of this invention is to eliminate these costly milk runs."

So-called "portable" oxygen concentrators are commercially available for providing patients with gaseous oxygen by converting ambient air into concentrated gaseous oxygen. However, these devices are only "portable" in the sense that they are capable of being transported to another point of use via an automobile or an airplane. One of these devices is packaged in a suitcase and is billed as a transportable machine rather than a truly portable oxygen concentrator. The device weighs about 37 lbs. without battery and requires 135 Watts of power at a 2 LPM (liters per minute) oxygen flow rate. Operation from an automobile battery is possible when in route in a car, but operation from a separate battery is impractical. Another device is a 3 LPM concentrator mounted on its own cart. It weighs 22 lbs. without battery and also requires about 135 Watts of power. A further device weighs about 28 lbs. without battery and has a similar flow rate and power requirements to the above devices. Even without a battery, these devices are too heavy for the average ambulatory respiratory patient. With the weight of a battery, these prior art devices are not "portable" in the true sense of the word because they can not be readily transported from one point to another. Because these devices have relatively large power consumption requirements, they also require a sizable battery.

Further, in addition to the weight and power consumption problems with the above oxygen concentrators, none of these prior art concentrators are particularly quiet. They produce noise levels similar to those produced by a home concentrator. In fact, one of these devices specifie's noise production at 60 dBA (decibels), about twice the noise of a home concentrator. Consequently, none of these so-called "portable" oxygen concentrators are suitable for use in environments where low noise is especially important, e.g., restaurants, libraries, churches and theatres.

Thus, a long-felt need exists for a truly "portable" oxygen concentration system that eliminates the need for high-pressure gas cylinders and liquid dewars, the constant refilling/replacing requirements associated with high-pressure gas cylinders and liquid dewars, and the need for a separate home oxygen concentration system for ambulatory respiratory patients. A truly "portable" oxygen concentration system would be light enough so that, even with a battery, an average ambulatory respiratory patient could carry the device. Inherently the device would have to be designed to have relatively low power consumption requirements so that a light-weight battery pack or other energy source could be used. Further, the device should be small enough so that it can be conveniently carried by the user, emit a relatively low amount of noise and should only emit a small amount of heat.

SUMMARY OF INVENTION

An aspect of the present invention involves a portable oxygen concentrator system adapted to be readily transported by a user. The portable oxygen concentrator system includes a rechargeable energy source and a concentrator powered by the energy source. The concentrator converts ambient air into concentrated oxygen gas for the user and includes a plurality of adsorption beds and a rotary valve assembly. The rotary valve assembly is relatively rotatable with respect to the plurality of adsorption beds to provide valving action for selectively transferring fluids through the plurality of adsorption beds for converting ambient air into concentrated oxygen gas for the user. The ratio of adiabatic power to oxygen flow for the concentrator is in the range of 6.2 W/LPM to 23.0 W/LPM.

Another aspect of the invention involves a rotary valve assembly for a pressure swing adsorption system having a plurality of adsorption beds. The rotary valve assembly includes a valve port plate and a rotary valve shoe having respective engaged surfaces and are relatively rotatable about a common center of rotation to provide valving action for selectively transferring fluids therethrough. The valve port plate includes at least two ports interconnected with at least two adsorption beds. The rotary valve shoe includes a second valve surface opposite the engaged surface with at least one equalization passage to register with the at least two ports of the port plate to equalize pressure between the at least two adsorption beds.

Other and further objects, features, aspects, and advantages of the present inventions will become better understood with the following detailed description of the accompanying drawings.

BRIEF DESCRIPTION OF THE DRAWINGS

FIG. 11 is a table of experimental data for a portable oxygen concentration system including the concentrator illustrated in FIGS. 3A and 3B.

FIG. 15 is a block diagram of a portable oxygen concentration system constructed in accordance with additional embodiment of the invention; and FIG. 16 is a schematic illustration of another embodiment of a portable oxygen concentration system including a high-pressure reservoir.

DETAILED DESCRIPTION OF THE PREFERRED EMBODIMENT

I. Portable Oxygen Concentration System

Figure 1:
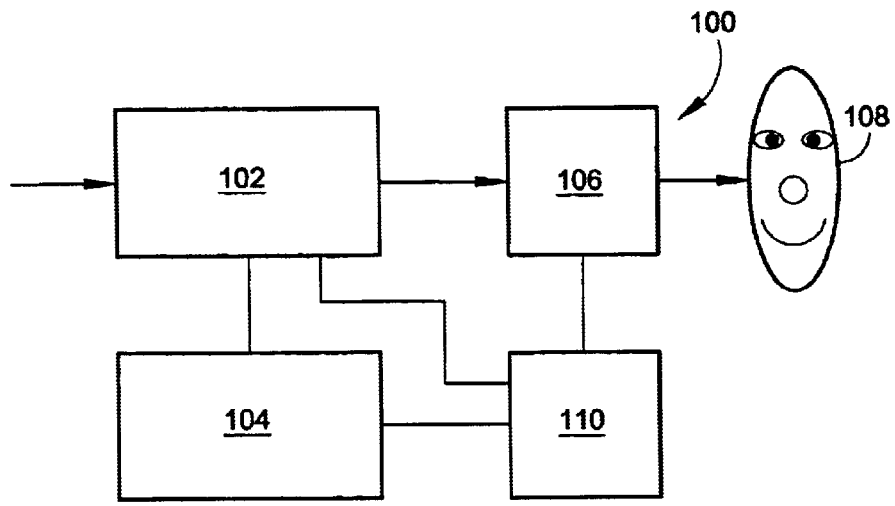
FIG. 1 is a block diagram of a portable oxygen concentration system constructed in accordance with an embodiment of the invention.

With reference to FIG. 1, a portable oxygen concentration system, indicated generally by the reference numeral 100, constructed in accordance with an embodiment of the invention will now be described. The oxygen concentration system 100 includes an air separation device such as an oxygen gas generator 102 that separates concentrated oxygen gas from ambient air, an energy source such as rechargeable battery, battery pack, or fuel cell 104 that powers at least a portion of the oxygen gas generator 102, one or more output sensors 106 used to sense one or more conditions of the user 108, environment, etc. to determine the oxygen output needed by the user or required from the system 100, and a control unit 110 linked to the output sensor 106, the air separation device 102, and the energy source 104 to control the operation of the air separation device 102 in response to the one or more conditions sensed by the one or more output sensors 106.

In an alternative embodiment, the system 100 may not include the one or more output sensors 106 coupled to the control unit 110. In this embodiment, conditions of the system 100 such as flow rate, oxygen concentration level, etc. may be constant for the system or may be manually controllable. For example, the system 100 may include a user interface 111 (FIG. 14) that allows the user, provider, doctor, etc. to enter information, e.g., prescription oxygen level, flow rate, etc. to control the oxygen output of the system 100.

Each element of the system 100 will now be described in more detail.

A. Air Separation Device

Figure 2:
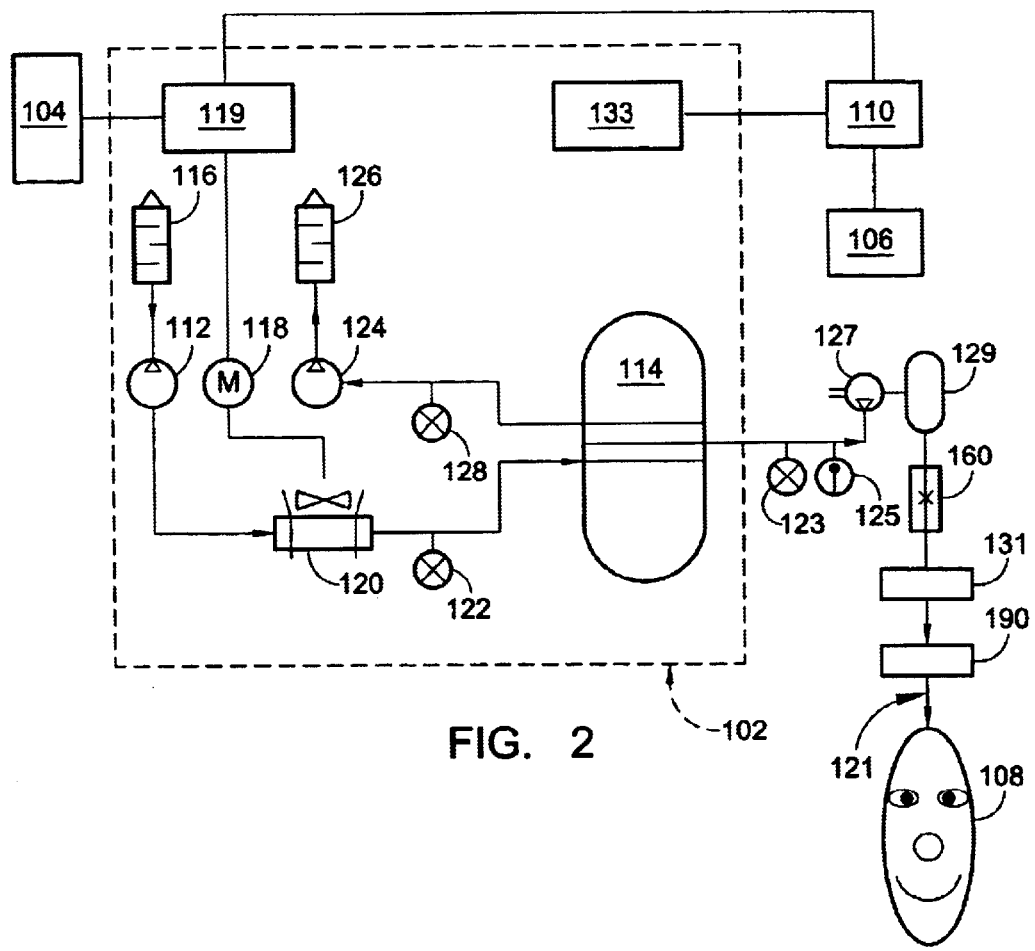
FIG. 2 is a block diagram of a portable oxygen concentration system constructed in accordance with another embodiment of the invention, and illustrates, in particular, an embodiment of an air separation device.

With reference to FIG. 2, the air separation device is preferably an oxygen generator 102 generally including a pump such as a compressor 112 and an oxygen concentrator 114 (OC), which may be integrated.

The oxygen generator 102 may also include one or more of the elements described below and shown within the segmented boundary line in FIG. 2. Ambient air may be drawn through an inlet muffler 116 by the compressor 112. The compressor 112 may be driven by one or more DC motors 118 (M) that run off of DC electrical current supplied by the rechargeable battery 104 (RB). The motor 118 also preferably drives the cooling fan part of the heat exchanger 120. A variable-speed controller (VSC) or compressor motor speed controller 119, which is described in more detail below, may be integral with or separate from the control unit 110 (CU) and is preferably coupled to the motor 118 for conserving electricity consumption. The compressor 112 delivers the air under pressure to the concentrator 114.

In a preferred embodiment, at a maximum speed air is delivered to the concentrator 114 at 7.3 psig nominal and may range from 5.3 to 12.1 psig. At maximum speed, the flow rate of feed is a minimum of 23.8 SLPM at inlet conditions of 14.696 psi absolute, 70 degrees F., 50% relative humidity.

A heat exchanger 120 may be located between the compressor 112 and the concentrator 114 to cool or heat the air to a desired temperature before entering the concentrator 114, a filter (not shown) may be located between the compressor 112 and the concentrator 114 to remove any impurities from the supply air, and a pressure transducer 122 may be located between the compressor 112 and the, concentrator 114 to get a pressure reading of the air flow entering the concentrator 114.

The concentrator 114 separates oxygen gas from air for eventual delivery to the user 108 in a well-known manner. One or more of the following components may be located in a supply line 121 between the concentrator 114 and the user 108: a pressure sensor 123, a temperature sensor 125, a pump 127, a low-pressure reservoir 129, a supply valve 160, a flow and purity sensor 131, and a conservation device 190. As used herein, supply line 121 refers to the tubing, connectors, etc. used to connect the components in the line. The pump 127 may be driven by the motor 118. The oxygen (gas may be stored in the low-pressure reservoir 129 and delivered therefrom via the supply line 121 to the user 108. The supply valve 160 may be used to control the delivery of oxygen gas from the low-pressure reservoir 129 to the user 108 at atmospheric pressure.

Exhaust gas may also be dispelled from the concentrator 114. In a preferred embodiment of the invention, a vacuum generator 124 (V), which may also be driven by the motor 118 and integrated with the compressor 112, draws exhaust gas from the concentrator 114 to improve the recovery and productivity of the concentrator 114. The exhaust gas may exit the system 100 through an exhaust muffler 126. A pressure transducer 128 may be located between the concentrator 114 and the vacuum generator 124 to get a pressure reading of the exhaust flow from the concentrator 114. At maximum rated speed and a flow rate of 20.8 SLPM, the pressure at the vacuum side is preferably −5.9 psig nominal and may range from −8.8 to −4.4 psig.

1. Compressor/Variable Speed Controller

Example of compressor technologies that may be used for the compressor 112 include, but not by way of limitation, rotary vane, linear piston with wrist pin, linear piston without wrist pin, nutating disc, scroll, rolling piston, diaphragm pumps, and acoustic. Preferably the compressor 112 and vacuum generator 124 are integrated with the motor 118 and are oil-less, preventing the possibility of oil or grease from entering the air flow path.

The compressor 112 preferably includes, at a minimum, a 3:1 speed ratio, with a low speed of at least 1,000 rpm and a 15,000 hour operating life when run at full speed. Operating temperature surrounding the compressor/motor system is preferably 32 to 122 degrees F. Storage temperature is preferably −4 to 140 degree F. Relative humidity is preferably 5 to 95% RH noncondensing. Voltage for the compressor 112 is preferably 12 V DC or 24V DC and the electrical power requirements are preferably less than 100 W at full speed and rated flow/nominal pressure and less than 40 W at ⅓ speed and ⅓ flow at rated pressure. A shaft mounted fan or blower may be incorporated with the compressor 112 for compressor cooling and possible complete system cooling. Preferably, the maximum sound pressure level of the compressor 112 may be 46 dBA at a maximum rated speed and flow/pressure and 36 dBA at ⅓ rated speed. Preferably the compressor 112 weighs less than 3.5 pounds.

It is desirable for the compressor 112 to run at a variety of speeds; provide the required vacuum/pressure levels and flow rates, emit little noise and vibration, emit little heat, be small, not be heavy, and consume little power.

The variable-speed controller 119 is important for reducing the power consumption requirements of the compressor 112 on the rechargeable battery 104 or other energy source. With a variable-speed controller, the speed of the compressor 112 may be varied with the activity level of the user, metabolic condition of the user, environmental condition, or other condition indicative of the oxygen needs of the user as determined through the one or more output sensors 106.

For example, the variable-speed controller may decrease the speed of the motor 118 when it is determined that the oxygen requirements of the user 108 are relatively low, e.g., when the user is sitting, sleeping, at lower elevations, etc., and increased when it is determined that the oxygen requirements of the user 108 are relatively high or higher, e.g., when the user stands, when the user is active, when the user is at higher elevations, etc. This helps to conserve the life of the battery 104, reduce the weight and size of the battery 104, and reduce the compressor wear rate, improving its reliability.

One of the inventors of the present invention was a co-inventor on a variable-speed controller in the past that regulated the compressor speed to operate the compressor only at the speed and power needed to deliver oxygen at the user's prescribed flow rate. This variable-speed controller is discussed in U.S. Pat. Nos. 5,593,478 and 5,730,778, which are hereby incorporated by reference as though set forth in full.

The variable-speed controller 119 allows the compressor 112 to operate at a low average rate, typically the average rate or speed will be between full speed and ⅙ full speed of the compressor 112, resulting in an increase in battery life, decrease in battery size and weight, and decrease in compressor noise and emitted heat.

2. Concentrator

In a preferred embodiment, the concentrator 114 is an Advanced Technology Fractionator (ATF) that may be used for medical and industrial applications. The ATF may implement a pressure swing adsorption (PSA) process, a vacuum pressure swing adsorption (VPSA) process, a rapid PSA process, a very rapid PSA process or other process. If a PSA process is implemented, the concentrator may include a rotating valve or a non-rotating valve mechanism to control air flow through multiple sieve beds therein. Examples of ATF concentrators are shown and described in U.S. Pat. Nos. 5,268,021, 5,366,541, Re. 35,099, which are hereby incorporated by reference as though set forth in full. The sieve beds may be tapered so that they have larger diameter where gaseous flow enters the beds and a smaller diameter where gaseous flow exits the beds. Tapering the sieve beds in this manner requires less sieve material and less flow to obtain the same output.

Although an ATF concentrator 114 is used in a preferred embodiment, it will be readily apparent to those skilled in the art that other types of concentrators or air-separation devices may be used such as, but not by way of limitation, membrane separation types and electrochemical cells (hot or cold). If other types of concentrators or air-separation devices are used, it will be readily apparent to those skilled in the art that some aspects described herein may change accordingly. For example, if the air-separation device is a membrane separation type, pumps other than a compressor may be used to move air through the system.

The ATF preferably used is significantly smaller that ATFs designed in the past. The inventors of the present invention recognized that reducing the size of the ATF concentrator 114 not only made the system 100 smaller and more portable, it also improved the recovery percentage, i.e., the percentage of oxygen gas in air that is recovered or produced by the concentrator 114 and the productivity (liters per minute/lb. of sieve material) of the concentrator 114. Reducing the size of the ATF decreases the cycle time for the device. As a result, productivity is increased.

Further, the inventors also determined that finer sieve materials increased recovery rates and productivity. The time constant to adsorb unwanted gases is smaller for finer particles because the fluid path is shorter for the gases than for larger particles. Thus, fine sieve materials having small time constants are preferred. An example of a sieve material that may be used in the ATF concentrator 114 is described in U.S. Pat. No. 5,413,625 to Chao, et al., which is incorporated by reference as though set forth in full. The sieve material may be a LithiumX Zeolite that allows for a high exchange of Lithium ions. The bead size may, for example, be 0.2–0.6 mm. In an alternative embodiment, the Zeolite may be in the form of a rigid structure such as an extruded monolith or in the form of rolled up paper. In this embodiment, the Zeolite structure would allow for rapid pressure cycling of the material without introducing significant pressure drop between the feed and product streams.

The size of the concentrator 114 may vary with the flow rate desired. For example, the concentrator 114 may come in a 1.5 Liter per minute (LPM) size, a 2 LPM size, a 2.5 LPM size, a 3 LPM size, etc.

The oxygen gas generator 102 may also include an oxygen source in addition to the concentrator 114 such as, but not by way of limitation, a high-pressure oxygen reservoir, as described in more detail below.

An ATF valve controller 133 may be integral with or separate from the control unit 110 and is coupled with valve electronics in the concentrator 114 for controlling the valve (s) of the concentrator 114.

The concentrator may have one or more of the following energy saving modes: a sleep mode, a conserving mode, and an active mode. Selection of these modes may be done manually by the user 108 or automatically such as through the described one or more sensors 106 and control unit 110.

Figure 3A:
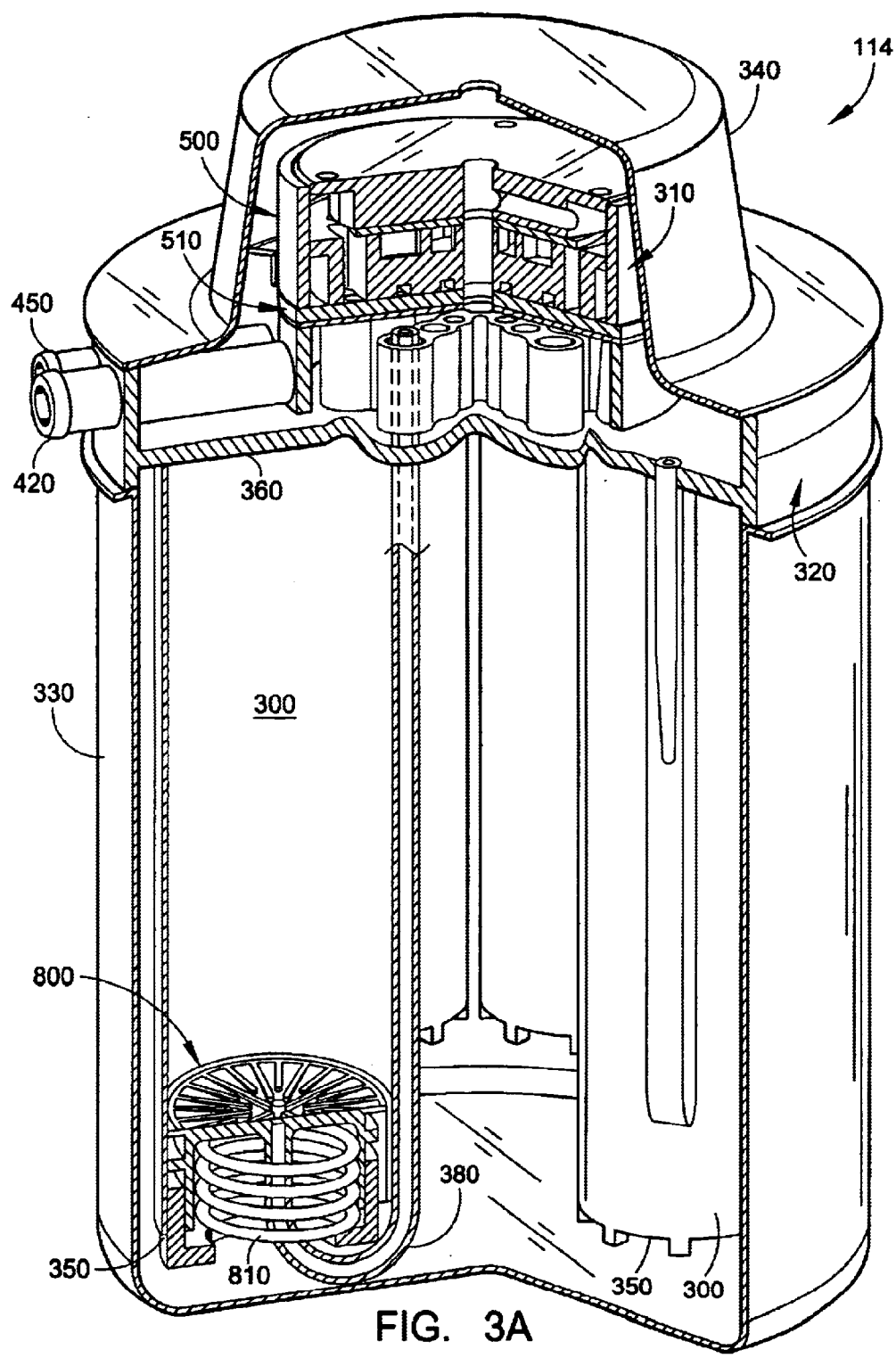
FIG. 3A is a perspective, cut-away view of an embodiment of a concentrator that may be used with the portable oxygen concentration system.
Figure 3B:
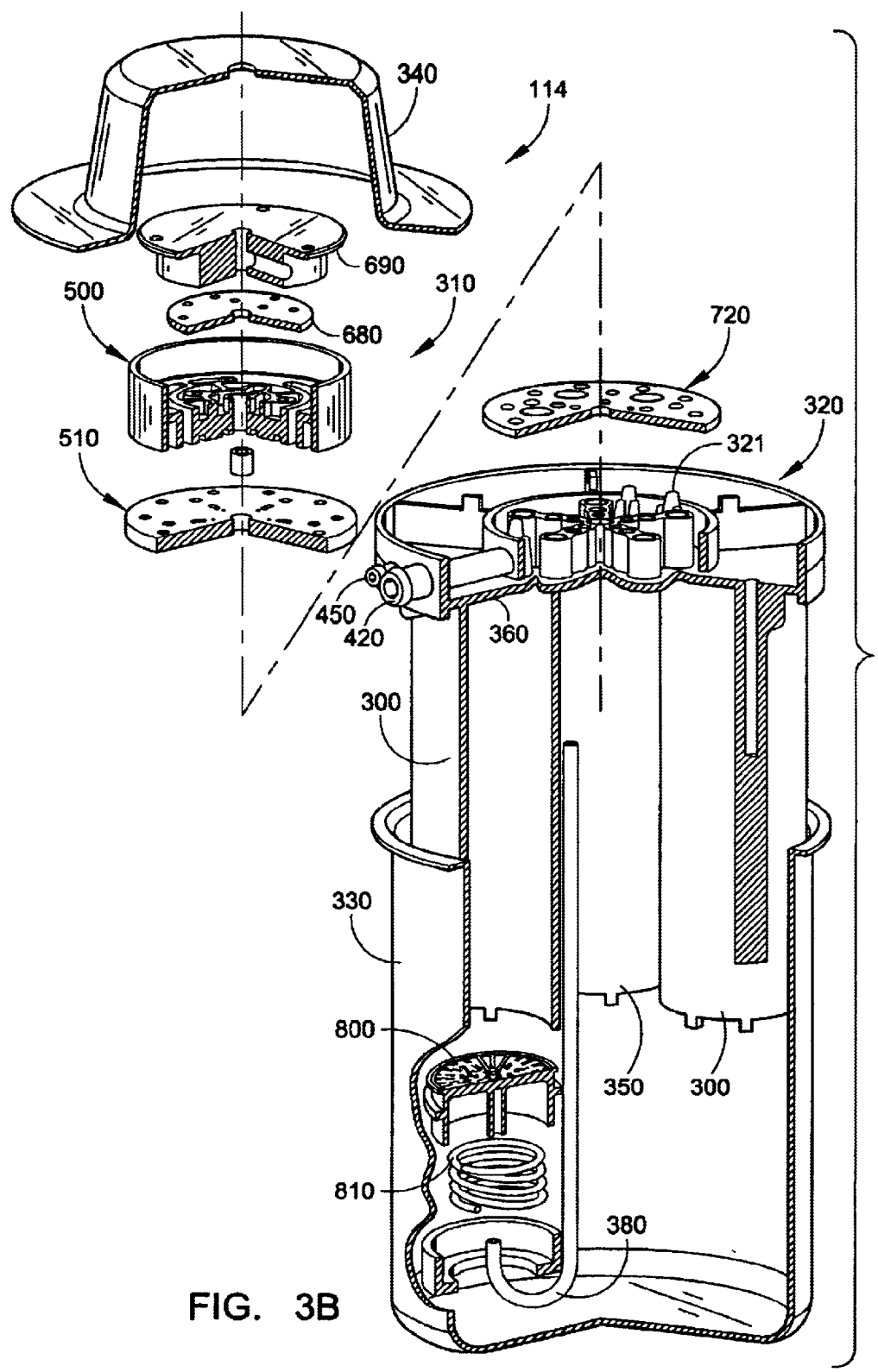
FIG. 3B is a perspective, exploded view of the concentrator illustrated in FIG. 3A.

With reference to FIGS. 3A and 3B, an embodiment of a concentrator 114 that may be used in the oxygen generator 102 will now be described in more detail. Although the concentrator 114 will be described as separating oxygen from air, it should be noted that the concentrator 114 may be used for other applications such as, but not by way of limitation, air separations for the production of nitrogen, hydrogen purification, water removal from air, and argon concentration from air. As used herein, the term "fluids" includes both gases and liquids.

The concentrator 114 described below includes numerous improvements over previous concentrators that result in increased recovery of the desired component and increased system productivity. Improved recovery is important since it is a measure of the efficiency of the concentrator. As a concentrator's recovery increases, the amount of feed gas required to produce a given amount of product decreases. Thus, a concentrator with higher recovery may require a smaller feed compressor (e.g., for oxygen concentration from air) or may be able to more effectively utilize feed gas to recover valuable species (e.g., for hydrogen purification from a reformate stream). Improved productivity is important since an increase in productivity relates directly to the size of the concentrator. Productivity is measured in units of product flow per mass or volume of the concentrator. Thus, a concentrator with higher productivity will be smaller and weigh less than a concentrator that is less productive, resulting in a more attractive product for many applications. Therefore, concentrator improvements in recovery, productivity, or both are advantageous. The specific improvements that lead to improved recovery and productivity are detailed below.

The concentrator 114 includes five adsorption beds 300, each containing a bed of adsorbent material which is selective for a particular molecular species of fluid or contaminant, a rotary valve assembly 310 for selectively transferring fluids through the adsorption beds 300, an integrated tube-assembly and mainifold "manifold" 320, a product tank cover 330, and a valve assembly enclosure 340.

The adsorption beds 300 are preferably straight, elongated, molded, plastic vessels surrounded by the product tank cover 330, which is made of metal, preferably aluminum. The molded, plastic adsorption beds 300 surrounded by the metal cover 330 make for a low-cost design without the detrimental effects of water influx that occur with prior-art plastic housings or covers. Plastic adsorption beds have the inherent problem of the plastic being permeable to water. This allows water to penetrate into the adsorbent material, decreasing the performance of the adsorbent material. Surrounding the plastic adsorption beds 300 with the aluminum cover 330, which also may serve as a product accumulation tank, maintains the low cost of the design and does not sacrifice performance.

Figure 4:
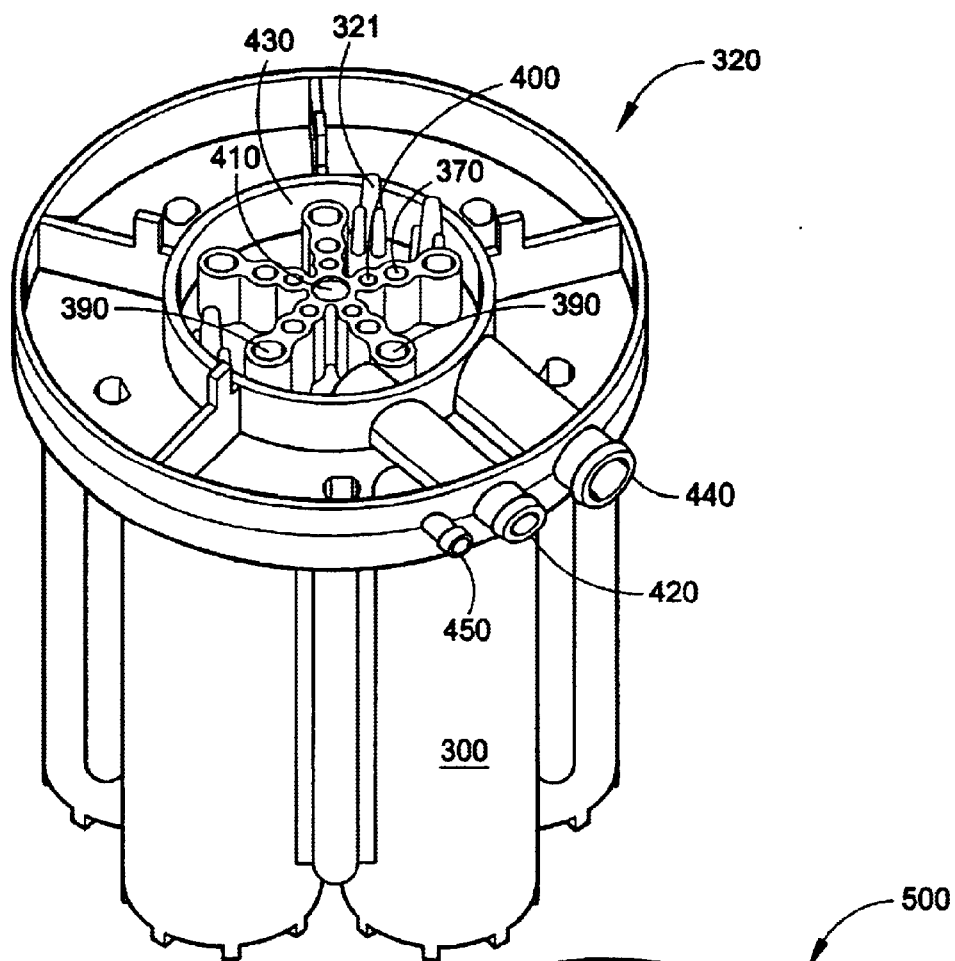
FIG. 4 is a top perspective view of an embodiment of a top manifold and multiple adsorption beds that may be used with the concentrator illustrated in FIGS. 3A and 3B.

Each adsorption bed 300 includes a product end 350 and a feed end 360. With reference additionally to FIG. 4, the product ends 350 of the beds 300 communicate with incoming product passages 370 of the manifold 320 through product lines 380 for communication with the rotary valve assembly 310. The feed ends 360 of the beds 300 communicate with outgoing feed passages 390 of the manifold 320 for communication with the rotary valve assembly 310.

The manifold 320 may also include outgoing product passages 400 that communicate the rotary valve assembly 310 with the interior of the product tank 330, an incoming feed passage 410 that communicates the rotary valve assembly 310 with a feed pressure line 420, and a vacuum chamber 430 that communicates the rotary valve assembly 310 with a vacuum pressure line 440. A product delivery line 450, which may be the same as the supply line 121 described above with respect to FIG. 2, communicates with the interior of the product tank 330. The vacuum pressure line 440 may communicate directly or indirectly with the vacuum generator 124 for drawing exhaust gas from the concentrator 114.

In use, air flows from the compressor 112 to the feed pressure line 420, through the incoming feed passage 410 of the manifold 320. From there, air flows to the rotary valve assembly 310 where it is distributed back through outgoing feed passages 390 of the manifold 320. From there, the feed air flows to the feed ends 360 of the adsorption beds 300. The adsorption beds 300 include adsorbent media that is appropriate for the species that will be adsorbed. For oxygen concentration, it is desirable to have a packed particulate adsorbent material that preferentially adsorbs nitrogen relative to oxygen in the feed air so that oxygen is produced as the non-adsorbed product gas. An adsorbent such as a highly Lithium exchanged X-type Zeolite may be used. A layered adsorbent bed that contains two or more distinct adsorbent materials may also be used. As an example, for oxygen concentration, a layer of activated alumina or silica gel used for water adsorption may be placed near the feed end 360 of the adsorbent beds 300 with a lithium exchanged X-type zeolite used as the majority of the bed toward the product end 350 to adsorb nitrogen. The combination of materials, used correctly, may be more effective than a single type of adsorbent. In an alternative embodiment, the adsorbent may be a structured material and may incorporate both the water adsorbing and nitrogen adsorbing materials.

The resulting product oxygen gas flows towards the products ends 350 of the adsorption beds 300, through the product lines 380, through incoming product passages 370 of the manifold 320, and to the rotary valve assembly 310, where it is distributed back through the manifold 320 via the outgoing product passage 400 and into the product tank 330. From the product tank 330, oxygen gas is supplied to the user 108 through the product delivery line 450 and the supply line 121.

With reference to FIGS. 3B, 5A, 5B, 6A, 8A, and 8B, an embodiment of the rotary valve assembly 310 will now be described. The rotary valve assembly 310 includes a rotary valve shoe or disk 500 and a valve port plate or disk 510. The rotary valve shoe 500 and valve port plate 510 are both preferably circular in construction and made from a durable material such as ceramic, which can be ground to a highly polished flat finish to enable the faces of the valve shoe 500 and port plate 510 to form a fluid-tight seal when pressed together.

Figure 5A:
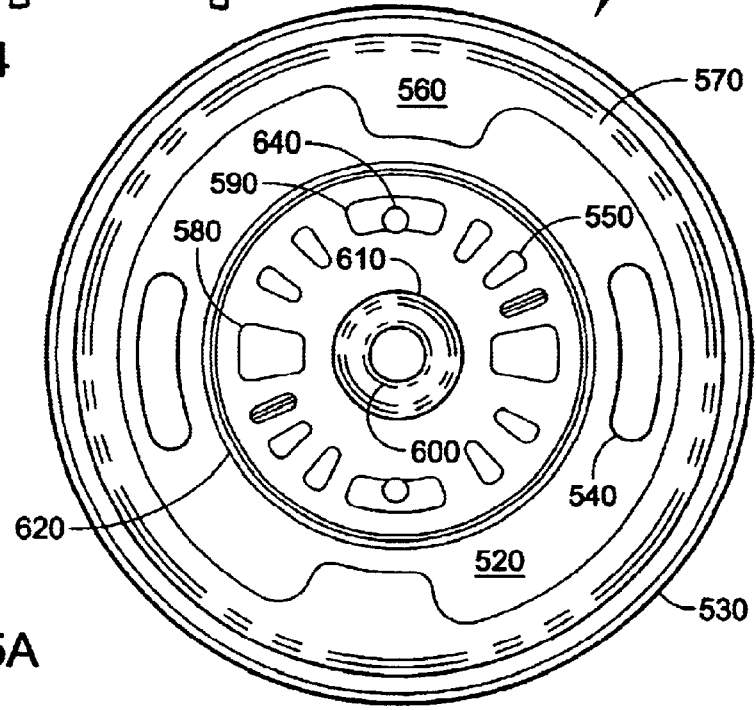
FIGS. 5A and 5B are a bottom plan view and a top plan view respectively of an embodiment of a rotary valve shoe that may be used with the concentrator illustrated in FIGS. 3A and 3B.

With reference specifically to FIG. 5A, the rotary valve shoe 500 has a flat, bottom engagement surface 520 and a smooth cylindrical sidewall 530. The valve shoe 500 has several symmetrical arcuate passages or channels cut into the engagement surface 520, all of which have as their center the geometric center of the circular engagement surface 520. The passages or channels include opposite high-pressure feed channels 540, equalization channels 550, opposite low-pressure exhaust passages 560, circular low-pressure exhaust groove 570 which communicates with exhaust passages 560, opposite product delivery channels 580, opposite purge channels 590, a high-presure central feed passage 600, a first annular vent groove 610, and a second annular vent groove 620.

Figure 5B:
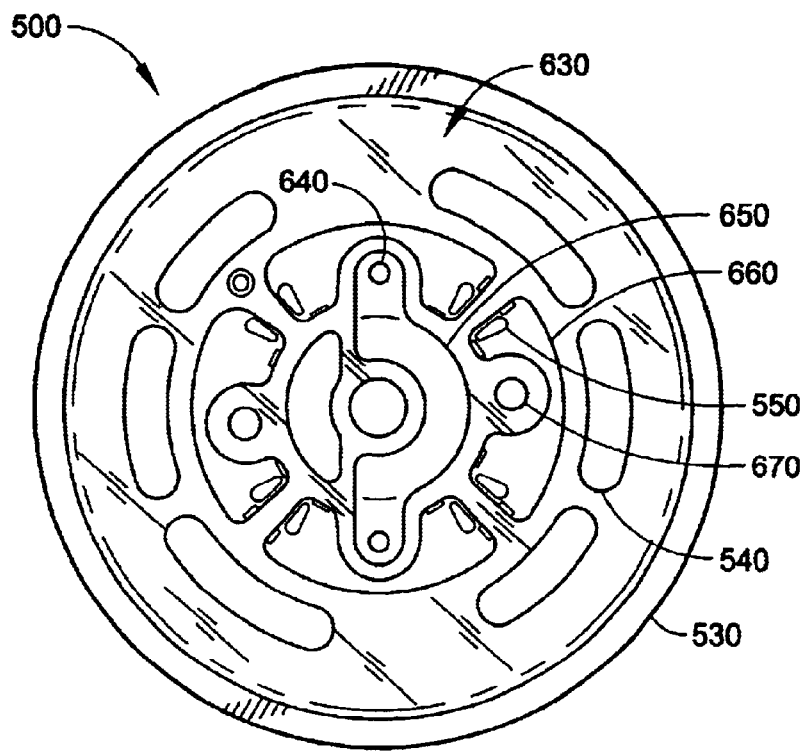

With reference additionally to FIG. 5B, a parallel, top, second valve surface 630 of the rotary valve shoe 500 will now be described. The purge channels 590 of the engagement surface 520 communicate with each other through vertical, cylindrical purge passages 640 and a rainbow-shaped purge groove 650 on the top surface 630. The equalization channels 550 of the engagement surface 520 extend vertically through the valve shoe 500. Pairs of equalization channels 550 communicate through equalization grooves 660 on the top surface 630. The equalization grooves 660 are generally U-shaped and extend around receiving holes 670. Equalization routing via the grooves 660 on the second valve surface 630, in a plane out of and parallel to a plane defined by the engagement surface 520, helps to maintain the relatively small size of the rotary valve shoe 500 while at the same time enabling more complex fluid routing through the valve shoe 500. The equalization grooves allow the secondary valve surface to be used to equalize pressures between adsorption beds 300.

Figure 8A:
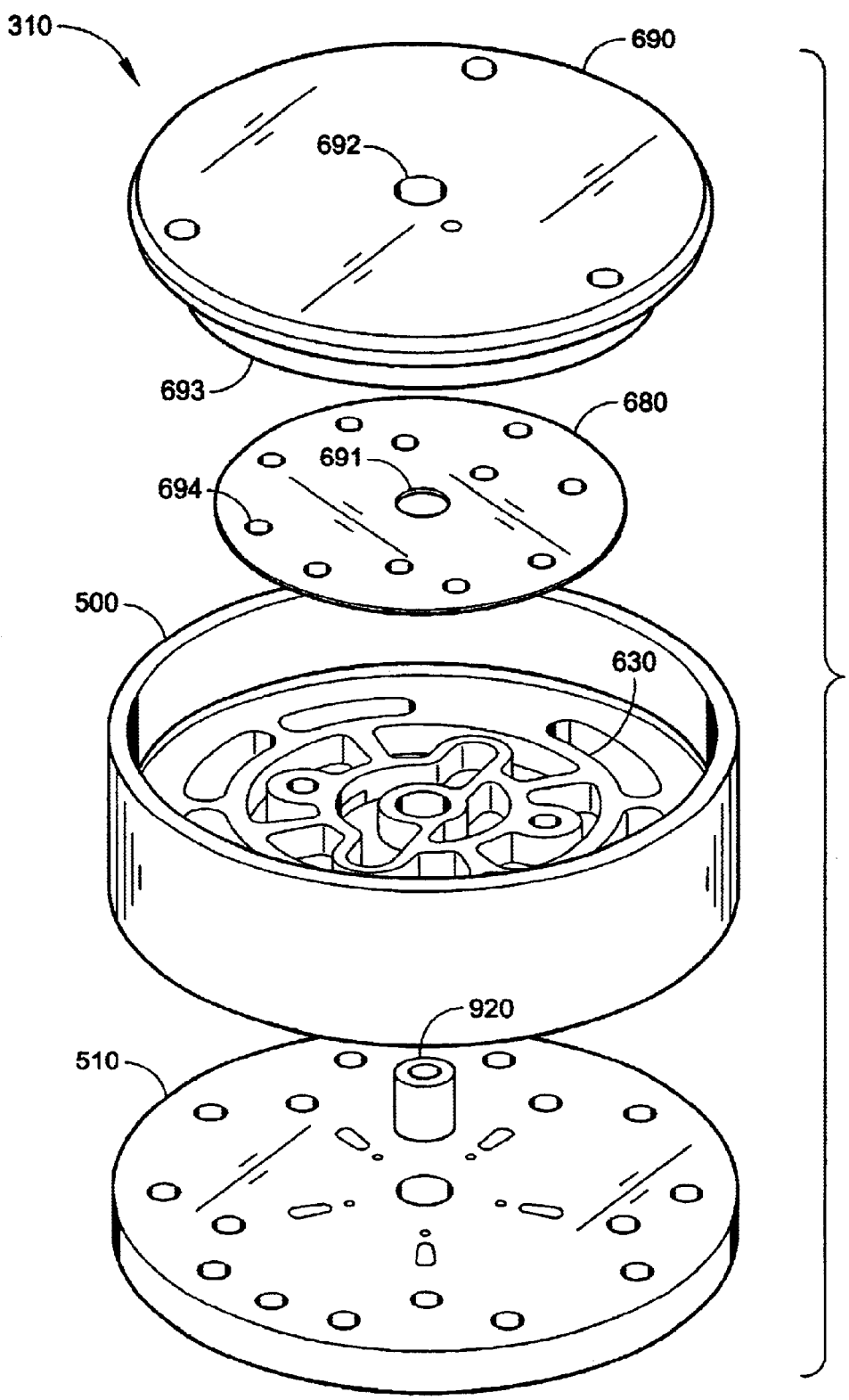
FIGS. 8A and 8B are a top perspective, exploded view and a bottom perspective, exploded view respectively of an embodiment of a rotary valve assembly including a centering pin that may be used with the concentrator illustrated in FIGS. 3A and 3B.
Figure 8B:
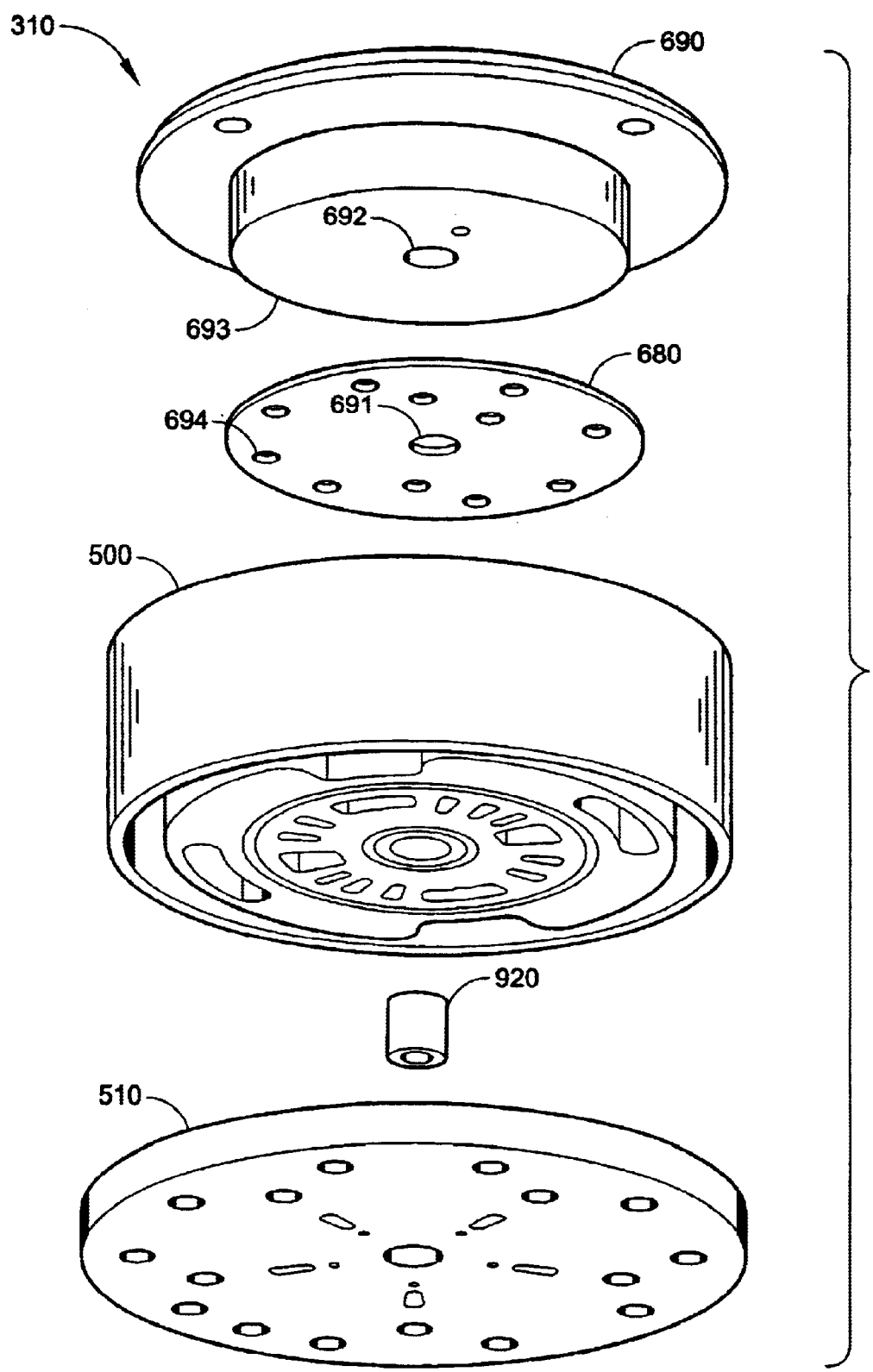

With reference to FIGS. 3B, 8A, and 8B, a first valve shoe cover 680 is disposed over the second valve surface 630 to isolate the various grooves and passages on the second valve surface 630. Both the first valve shoe cover 680 and the second valve shoe cover 690 include aligned central holes 691, 692, respectively, for communicating the central feed passage 600 with a high-pressure feed fluid chamber formed around the periphery of a cylindrical base 693 of the second valve shoe cover 690. The first valve shoe cover 680 also includes a plurality of holes 694 near its periphery for the purpose of maintaining a balance of pressure during operation on either side of the first valve shoe cover 680 between the cylindrical base 693 and the second valve surface 630. Routing the high-pressure feed fluid into the high-pressure feed fluid chamber on the top or backside of the valve shoe 500 causes pressure balancing on the valve shoe 500 that counteracts the pressure force urging the valve shoe 500 away from the port plate 510. A spring or other type of passive sealing mechanism (not shown) may be used to hold the rotary valve shoe 500 against the port plate 510 when the concentrator 114 is not operating.

With reference to FIG. 5A, to additionally counteract the pressure force that works to unseat the rotary valve shoe 500 from the port plate 510, the exhaust goove 570 is sized such that, when the concentrator 114 is operated at nominal feed and purge (vacuum) pressures, the sealing force due to the vacuum in the exhaust groove 570 subtantially balances this unseating pressure force. This enables the use of relatively small passive sealing mechanisms, reducing the torque and power required to turn the rotary valve shoe 500 and also reduces the weight and size of the concentrator 114.

Figure 6A:
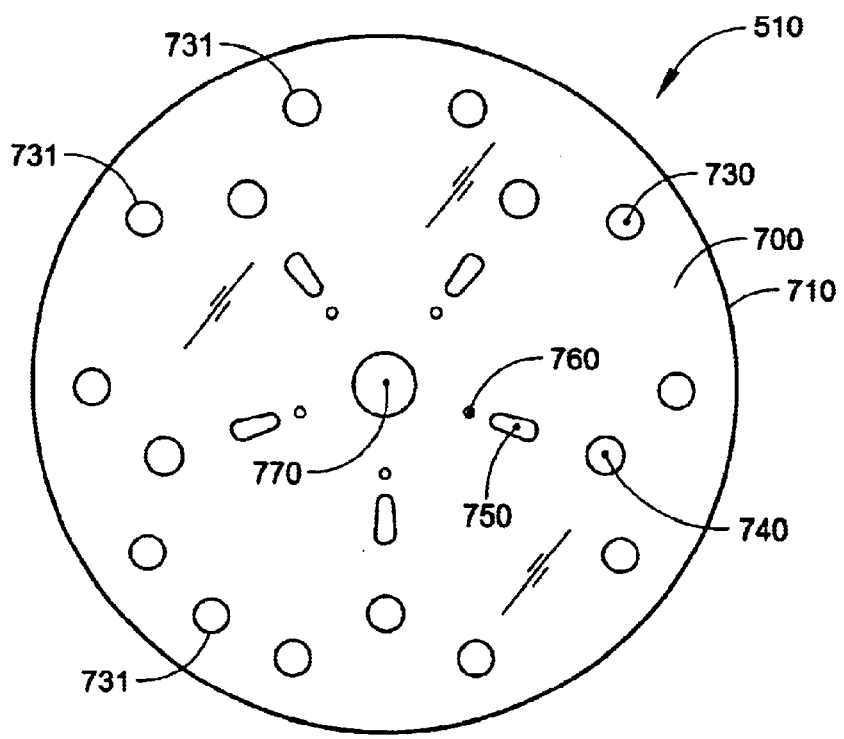
FIG. 6A is a top plan view of an embodiment of a valve port plate that may be used with the concentrator illustrated in FIGS. 3A and 3B.

With reference to FIG. 6A, the valve port plate 510 will now be described in greater detail. The valve port plate 510 has a flat engagement surface 700 that engages the flat engagement surfce 520 of the rotary valve shoe 500 and a smooth cylindrical sidewall 710. With reference additionally to FIG. 3B, an underside of the valve port plate 510 is disposed on a manifold gasket 720. The valve port plate 510 includes multiple sets of generally symmetric concentrically disposed ports or openings aligned with openings in the manifold gasket 720 to communicate the ports in the plate 510 with the passages in the manifold 320. The ports extend vertically through the valve port plate 510 in a direction generally perpendicular to the engagement surface 700. In an alternative embodiment, the ports extend vertically through the valve port plate 510 in an angular direction toward the engagement surface 700. Preferably, all of the ports of each concentric set have the same configuration. Each concentric set of ports will now be described in turn.

A first set of eight circular vacuum ports 730 concentrically disposed at a first radius from the geometric center of the valve port plate 510 communicate with the vacuum chamber 430 of the manifold 320 and the exhaust gas grooves 570 of the valve shoe 500. In the prefered embodiment, eight ports are used as they allow sufficient gas flow through the valve without significant pressure drop. In an alternative embodiment, a number of ports different from eight could be used.

A second set of five round outgoing feed ports 740 concentrically disposed at a second radius from the geometric center of the valve port plate 510 communicate with outgoing feed passages 390 of the manifold 320, the feed channels 540 of the valve shoe 500, and the vacuum ports 730 via the exhaust passages 560 of the valve shoe 500.

A third set of five generally elliptical incoming product ports 750 concentrically disposed at a third radius from the geometric center of the valve port plate 510 communicate with the incoming product passages 370 of the manifold 320, the equalization channels 550 of the valve shoe 500, the purge channels 590 of the valve shoe 500, and the product delivery channels 580.

A fourth set of five circular outgoing product ports 760 concentrically disposed at a fourth radius from the geometric center of the valve port plate 510 communicate with the outgoing product passages 400 of the manifold 320 and the incoming product ports 750 via the product delivery channels 580.

A fifth set of three circular port plate alignment holes 731 concentrically disposed at a fifth radius from the geometric center of the valve port plate 510 align with alignment pins 321 (FIGS. 3B, 4) on the manifold 320. The alignment holes 731 ensure the port plate 510 will sit in proper alignment with the manifold 320. In an alternative embodiment, two or more alignment holes located at one or more radiuses from the geometric center of the valve port plate 510 may be aligned with an equal number of alignment pins located at set positions on the manifold 320.

A round central incoming feed port 770 disposed at the geometric center of the valve port plate 510 and the center of rotation of the valve assembly 310 communicates with the incoming feed passage 410 of the manifold 320 and the central feed pasage 600 of the rotary valve shoe 500.

In the rotary valve assembly 310 described above, a maximum of 1 PSI pressure drop occurs through any port of the valve asembly 310 when the system is producing 3 LPM of oxygen product. At lesser flows, the pressure drop is negligible.

Figure 6B:
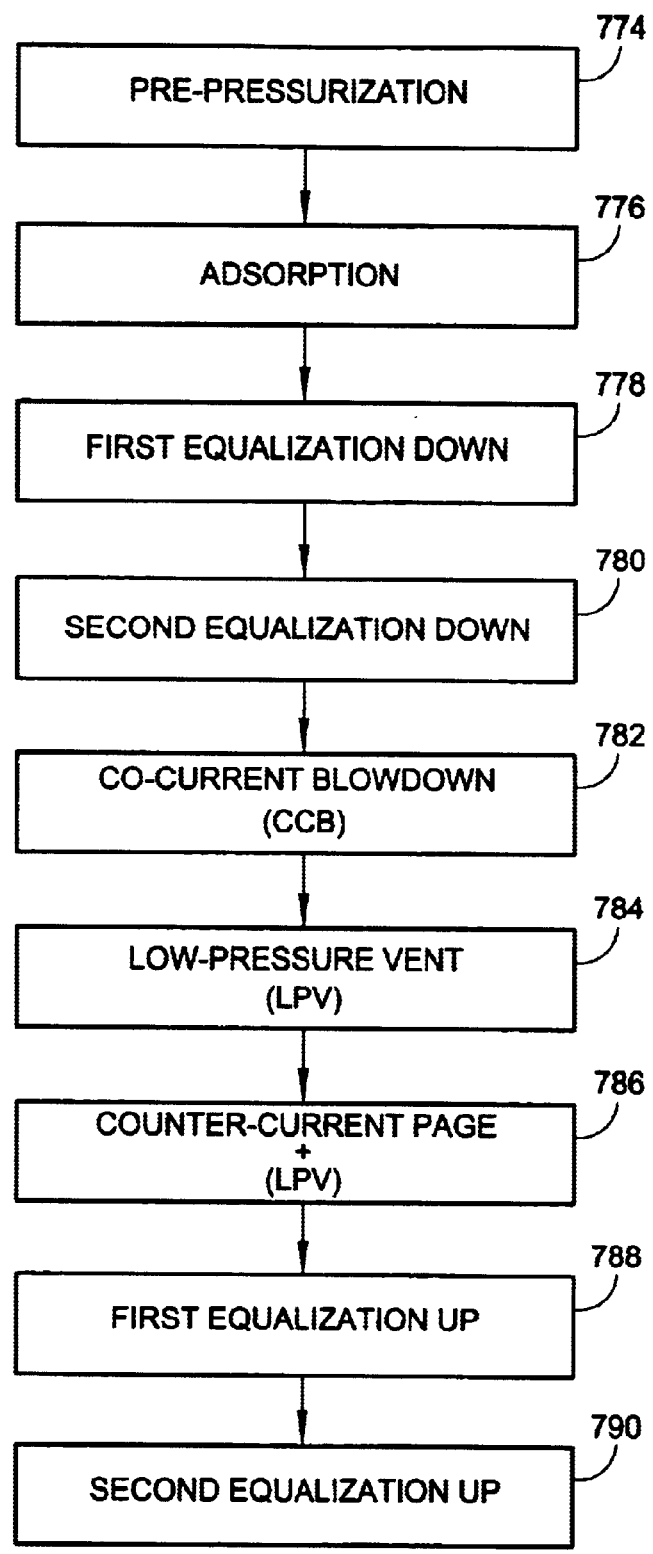
FIG. 6B is a flow chart of an exemplary process cycle for the concentraotor illustrated in FIGS. 3A and 3B.

With reference additionally to FIG. 6B, a single pressure swing adsorption cycle of the concentrator 114 will now be described. During use, the rotary valve shoe 500 rotates with respect to the valve port plate 510 so that the cycle described below is sequentially and continuously established for each adsorption bed 300. The speed of rotation of the rotary valve shoe 500 with respect to the valve port plate 510 may be varied alone, or in combination with a variable-speed compressor, in order to provide the optimal cycle timing and supply of ambient air for a given production of product. To help the reader gain a better understanding of the invention, the following is a description of what occurs in a single adsorption bed 300 and the rotary valve assembly 310 during a single cycle. It should be noted, with each revolution of the rotary valve shoe 500, the adsorption beds 300 undergo two complete cycles. For each cycle, the steps include: 1) pre-pressurization 774, 2) adsorption 776, 3) first equalization down 778, 4) second equalization down 780, 5) co-current blowdown 782, 6) low-pressure venting 784, 7) counter-current purge and low-pressure venting 786, 8) first equalization up 788, and 9) second equalization up 790.

Each of these steps will be described in turn below for an adsorption bed 300.

In the pre-pressurization step 774, air flows from the compressor 112 to the feed pressure line 420, through the incoming feed passage 410 of the manifold 320. From there, air flows through the central incoming feed port 770 of the port plate 510, through the central feed passage 600 and out the feed channels 540 of the valve shoe 500, through the outgoing feed ports 740, and through outgoing feed passages 390 of the manifold 320. From there, the feed air flows to the feed ends 360 of the adsorption beds 300. With reference to FIG. 5A, because the feed channel 540 is advanced with respect to the product delivery channel 580 (i.e., initially the feed channel 540 is in communication with outgoing feed port 740 and the product delivery channel 580 is blocked, not in communication with the incoming product port 750), the feed end 360 of the adsorption bed 300 is pressurized with feed gas, i.e., pressurized, prior to the commencement of product delivery. In alternative embodiments, the product end 350 may be pre-pressurized with product gas, or the product end 350 may be pre-pressurized with product gas and the feed end 360 may be pre-pressurized with feed gas.

In the adsorption step 776, because the product delivery channel 580 is in communication with the incoming product port 750, adsorption of Nitrogen occurs in the bed 300 and the resulting product oxygen gas flows towards the product ends 350 of the adsorption beds 300, through the product lines 380, and through incoming product passages 370 of the manifold 320. From there, oxygen gas flows through the incoming product port, into and out of the product delivery channel 580, through outgoing product port 760, through the outgoing product passage 400, and into the product tank 330. From the product tank 330, oxygen gas is supplied to the user 108 through the product delivery line 450 and the supply line 121.

In the first equalization-down step 778, the product end 350 of the bed 300, which is at a high pressure, is equalized with the product end of another bed, which is at a low pressure, to bring the product end 350 of the bed 300 to a lower, intermediate pressure. The product ends 350 communicate through the product lines 380, the incoming product passages 370, the incoming product ports 750, the equalization channels 550, and the equalization groove 660. As indicated above, equalization routing via the grooves 660 on the second valve surface 630, in a plane out of and parallel to a plane defined by the engagement surface 520, helps to maintain the relatively small size of the rotary valve shoe 500, in order to keep the torque required to turn the valve shoe 500 as low as possible, while at the same time enabling more complex fluid routing through the valve shoe 500. In this step 778 and the equalization steps 780, 788, 790 to be discussed below, the adsorption beds 300 may be equalized at either the feed end 360, the product end 350, or a combination of the feed end 360 and the product end 350.

In the second equalization-down step 780, the product end 350 of the bed 300, which is at an intermediate pressure, is equalized with the product end of another bed, which is at a lower pressure, to bring the product end 350 of the bed 300 further down to an even lower pressure than in step 778. Similiar to the first equalization-down step 778, the product ends 350 communicate through the product lines 380, the incoming product passages 370, the incoming product ports 750, the equalization channels 550, and the equalization groove 660.

In the co-current blowdown ("CCB") step 782, oxygen enriched gas produced from the product end 350 of the adsorption bed 300 is used to purge a second adsorption bed 300. Gas flows from the product side of the adsorption bed 300, through product line 380, incoming product passage 370, and incoming product port 750. The gas further flows through purge channel 590, purge passage 640, through the purge groove 650, out the purge passage 640 on the opposite side of the valve shoe 500, through the purge channel 590, through the incoming product port 750, through the incoming product pasasge 370, through the product line 380, and into the product end 350 of adsorption bed 300 to serve as a purge stream. In an alternative embodiment, in this step 782 and the following step 784, co-current blowdown may be replaced with counter-current blowdown.

In the low-pressure venting ("LPV") step 784, the adsorption bed 300 is vented to low pressure through the feed end 360 of the adsorption bed 300. The vacuum in the exhaust groove 570 of the rotary valve shoe 500 communicates with the exhaust passage 560 and the feed end 360 of the adsorption bed 300 (via the outgoing feed port 740 and outgoing feed passage 390) to draw the regeneration exhaust gas out of the adsorption bed 300. The low pressure venting step 784 occurs without introduction of oxygen enriched gas because the exhaust passage 560 is in communication with the outgoing feed port 740 and the purge channel 590 is not in communication with the incoming product port 750.

In the counter-current purge and low-pressure venting ("LPV") step 786, oxygen enriched gas is introduced into the product end 350 of the adsorption bed 300 in the manner described above in step 782 concurrently with the feed end 360 of the adsorption bed 300 being vented to low pressure as was described in the above step 784. Counter-current purge is introduced into the product end 350 of the adsorbent bed 300 through fluid communication with the product end 350 of a second adsorption bed 300. Oxygen enriched gas flows from the product end 350 of the second adsorption bed 300 through the product line 380, incoming product passage 370, incoming product port 750, through purge channel 590, purge passage 640, through the purge groove 650, out the purge passage 640 on the opposite side of the valve shoe 500, through the purge channel 590, through the incoming product port 750, through the incoming product passage 370, through the product line 380, and into the product end 350 of adsorption bed 300. Because the exhaust passage 560 is also in communication with the outgoing feed port 740 during this step 786, oxygen enriched gas flows from the product end 350 to the feed end 360, regenerating the adsorption bed 300. The vacuum in the exhaust groove 570 of the rotary valve shoe 500 communicates with the exhaust passage 560 and the feed end 360 of the adsorption bed 300 (via the outgoing feed port 740 and outgoing feed passage 390) to draw the regeneration exhaust gas out of the adsorption bed 300. From the exhaust passage 560, the exhaust gas flows through the vacuum ports 730, into the vacuum chamber 430, and out the vacuum presure line 440. In an alternative embodiment, the vacuum may be replaced with a low-pressure vent that is near atmospheric pressure or another pressure that is low relative to the feed pressure. In another embodiment, product gas from the product tank 330 is used to purge the product end 350 of the adsorbent bed 300.

In the first equalization-up step 788, the product end 350 of the bed 300, which is at a very low pressure, is equalized with the product end of another bed, which is at a high pressure, to bring the adsorption bed 300 to a higher, intermediate pressure. The product ends 350 communicate through the product lines 380, the incoming product passages 370, the incoming product ports 750, the equalization channels 550, and the equalization groove 660.

In the second equalization-up step 790, the product end 350 of the bed 300, which is at an intermediate pressure, is equalized with the product end of another bed, which is at a higher pressure, to bring the product end 350 of the bed 300 further up to an even higher pressure than in step 788. Similiar to the first equalization-down step 778, the product ends 350 communicate through the product lines 380, the incoming product passages 370, the incoming product ports 750, the equalization channels 550, and the equalization groove 660.

It should be noted, in a preferred embodiment, the combined duration of feed steps 774, 776 may be substantially the same as the combined duration of purge steps 782, 784, 786, which may be substantially three times the duration of each equalization step 778, 780, 788, 790. In an alternative embodiment, the relative duration of the feed steps 774, 776, the purge steps 782, 784, 786, and the each equalization step 778, 780, 788, 790 may vary.

After the second equalization-up step 790, a new cycle begins in the adsorption bed 300 starting with the pre-pressurization step 774.

The five-bed concentrator 114 and cycle described above has a number of advantages over other-numbered concentrators and cycles used in the past, some of which are described below. The multiple equalization steps 788, 790 at the product ends 350 and the pre-pressurization step 774 contribute to the pre-pressurization of the adsorption beds 300 prior to product delivery. As a result, the beds 300 reach their ultimate pressure (substantially equal to the feed pressure) quickly and thereby allow for maximum utilization of the adsorbent media. Additionally, pre-pressurizing the adsorbent beds 300 allows product to be delivered at substantially the same pressure as the feed, thereby retaining the energy of compression in the stream, which makes the product stream more valuable for use in downstream processes. In an alternative embodiment, pre-pressurizing the beds 300 with product before exposing the feed end 360 of the bed 300 to the feed stream eliminates any pressure drop experienced due to the fluid interaction or fluid communication between two or more adsorbent beds 300 on the feed end 360. Additionally, compared to systems with greater numbers of beds, the use of a 5-bed system, reduces the duration and number of beds that are in fluid communication with the feed chanels 540 at the same time, thereby reducing the propensity for fluid flow between adsorption beds. Since fluid flow between adsorption beds is associated with a reversal of the flow direction in the higher pressure bed (resulting in decreased performance), reduction in this effect is advantageous.

A further advantage of a 5-bed system over many systems is that it includes a small number of adsorption beds 300, allowing the concentrator to be relative small, compact, and light-weight, while delivering sufficient flow and purity and maintaining high oxygen recovery. Other PSA systems, typically those with a small number of adsorption beds, result in deadheading the compressor (resulting in high power use) during a portion of the cycle. Deadheading the compressor eliminates detrimental flow between the feed side 360 of the two or more adsorption beds 300 (as discussed above) but increases system power. The 5-bed system eliminates compressor deadheading and minimizes performance-limiting feed side 360 flow between adsorbent beds 300.

Use of the multiple pressure equalization steps 778, 780, 788, 790 reduces the amount of energy of compression required to operate the concentrator 114. Equalizing the beds 300 conserves high-pressure gas by moving it to another bed 300 rather than venting it to the atmosphere or to a vacuum pump. Because there is a cost associated with pressurizing a gas, conserving the gas provides a savings and improves recovery. Also, because a bed 300 may contain gas enriched with product, usually at the product end 350 of the bed 300, allowing this gas to move into another bed 300, rather than venting it, conserves product and improves recovery. The number of equalizations are preferably between one and four. It should be noted, each equalization represents two equalization steps, an equalization-down step and an equalization-up step. Thus, two equalizations means two down equalizations and two up equalizations, or four total equalizations. The same is true for other-number equalizations. In a preferred embodiment, one to four equalizations (two to eight equalization steps) are used in each cycle. In a more preferred embodiment, one to three equalizations (two to six equalization steps) are used in each cycle. In a most preferred embodiment, two equalizations (four equalization steps) are used in each cycle.

In alternative embodiments, the concentrator 114 may have other numbers of adsorption beds 300 based on the concentration of the feed stream, the specific gases to be separated, the pressure swing adsorption cycle, and the operating conditions. For example, but not by way of limitation, there also are advantages to four-bed concentrators and six-bed concentrators. When operating a cycle similar to that described above with a four-bed concentrator, the problem of fluid communication between the feed chanels 540 and more than one adsorption bed (at one instant) is completely eliminated. When the feed-end fluid communication is eliminated, the feed steps 774, 776 occur in a more desirable fashion resulting in improved recovery of the desired product. The advantages of a six-bed system, compared to a five-bed system, are realized when the pressure-swing cycle described above is modified so that there are three equalization up stages and three equalization down stages instead of two equalization up stages and two equalization down stages. A third equalization is advantageous when the feed gas is available at high pressure. The third equalization conserves compressor energy because it allows the equalized beds to obtain substantially 75% of the feed pressure compared to substantially 67% of the feed pressure when two equalization stages are used. In any PSA cycle, whenever an equalization up occurs, there is a corresponding equalization down. The requirement of matching equalization stages inparts some restrictions on the relative timing of the cycle steps. If, for example, the duration of the feed step is substantially the same as the duration of each equalization step, then a six-bed cycle would provide the required matching of equalization stages.

A number of additional inventive aspects related to the concentrator 114 that increase recovery of a desired component and system productivity will now be described. With reference to FIGS. 3A, 3B, 7A, and 7B, an embodiment of a media retention cap 800 that reduces dead volume in the adsorption beds 300 will now be described. Each media retention cap 800 is located at the product end 350 of the adsorption bed 300 and supports the adsorbent material above the media retention cap 800. A spring 810 located within and below the media retention cap 800 urges the media retention cap 800 upwards to hold the packed bed of adsorbent material firmly in place. The media retention cap 800 has a cylindrical base 820 with first and second annular flanges 830, 840. The second annular flange 840 terminates at its top in a circular rim 850. A top surface 860 of the media retention cap 800 includes a plurality of ribs 870 radiating in a generally sunburst pattern from a central port 880. Adjacent the central port 880, gaps 890 create diffusion zones for purge fluid coming out of the central port 880. The gaps 890 and the radiating ribs 870 cause the purge fluid to be distributed outward from the central port 880, causing a more uniform, improved regeneration of the adsorbent material during a purging step. The radiating ribs 870 also help to channel product gas towards the central port 880 during a product delivery step. In an alternative embodiment, the media retention cap 800 may have a generally non-cylindrical surface to retain media in a generally non-cylindrical adsorbtion bed 300. In a further alternative embodiment, the central port 880 may be located away from the geometric center of the either cylindrical or non-cylindrical media retention cap 800.

Figure 7A:
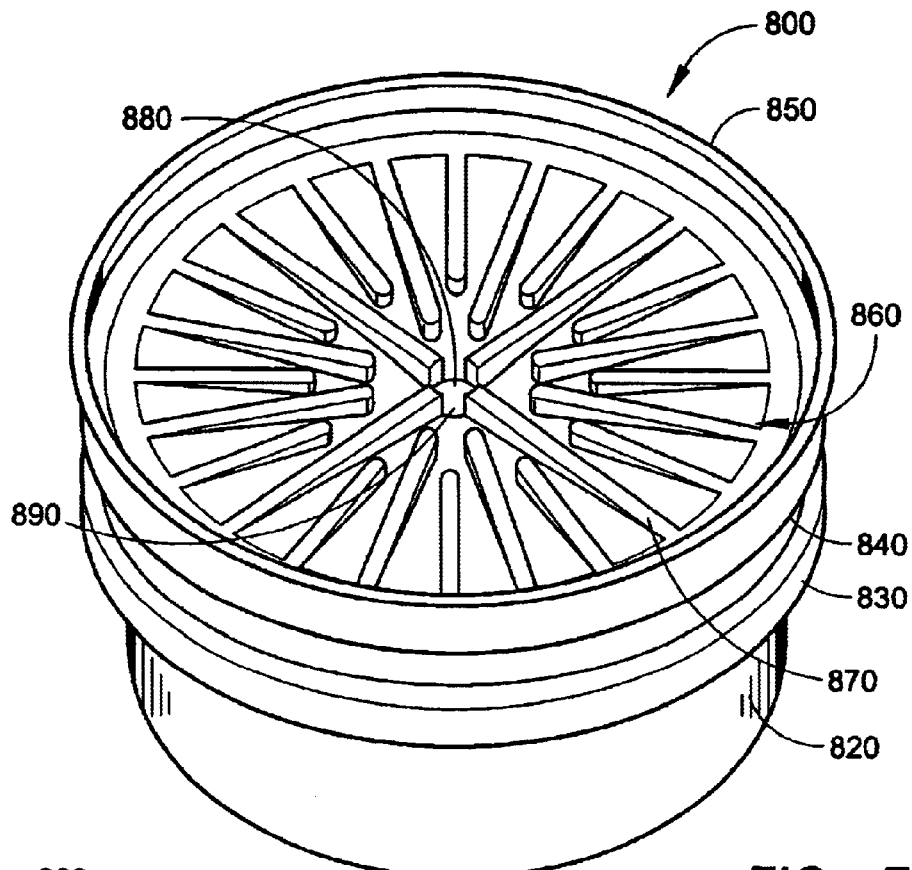
FIGS. 7A and 7B are a top plan view and a bottom plan view respectively of an embodiment of a media retention cap that may be used with the concentrator illustrated in FIGS. 3A and 3B.
Figure 7B:
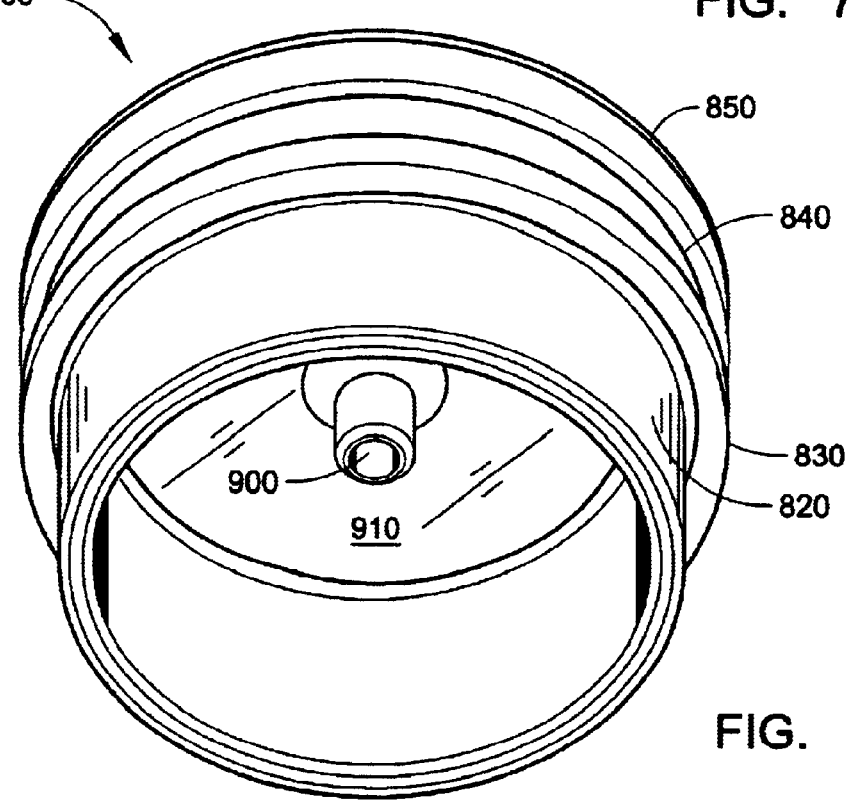

With reference to FIG. 7B, on the underside of the media retention cap 800, the cydrical base 820 forms an interior chamber in which the spring 810 is disposed. A central port nipple 900 extends from a bottom surface 910 of the media retention cap 800. An end of the product line 380 connects to the central port nipple 900 for communicating the product end 350 of the adsorption bed 300 with the incoming product passage 370 of the manifold 320.

In the past, media retention caps may be held in place with a spring that fits inside and above the cap so that the spring is in the fluid flow path between the bottom of the adsorbent material and any exit port, at the product end 350 of the bed 300. The volume in which the spring is housed represents dead volume in the system. As used herein, "dead volume" is system volume that is compressed and purged, but does not contain adsorbent media. The process of filling this volume with compressed feed and then venting that volume represents wasted feed. The improved media retention cap 800 does not add dead volume to the system because the spring 810 is housed outside of the fluid flow path. Elimination of any extra volume within the system results directly in more effective utilization of the feed, and, thus, higher recovery of the desired product.

With reference to FIGS. 8A and 8B, an embodiment of a centering mechanism for maintaining the rotary valve shoe 500 laterally fixed and centered with respect to the valve port plate 510 will now be described. The centering mechanism may include a centering pin 920 having a hollow cylindrical shape and made of a rigid material. When the engagement surface 520 of the rotary valve shoe 500 is engaged with the engagement surface 700 of the valve port plate 510, the centering pin 920 is partially disposed in the central feed pasage 600 of the rotary valve shoe 500 and the central incoming feed port 770 of the valve port plate 510. In use, the rotary valve shoe 500 rotates around the centering pin 920 and the hollow interior of the centering pin 920 allows high-pressure feed fluid to flow therethrough. The pin 920 maintains the rotating valve shoe in a fixed position relative to the valve port plate 510. In the past, the rotary valve shoe was roughly centered with respect to the valve port plate by the motor that drives the rotary valve shoe. If the rotary valve shoe 500 and the valve port plate 510 are off center with respect to each other, the concentrator 114 will not cycle as intended, inhibiting the productivity, recovery, and efficiency of the concentrator. The precision offered by the centering pin 920 is important when the valve assembly 310 is controlling complex cycles or maintaining very small pressure drops.

Figure 9A:
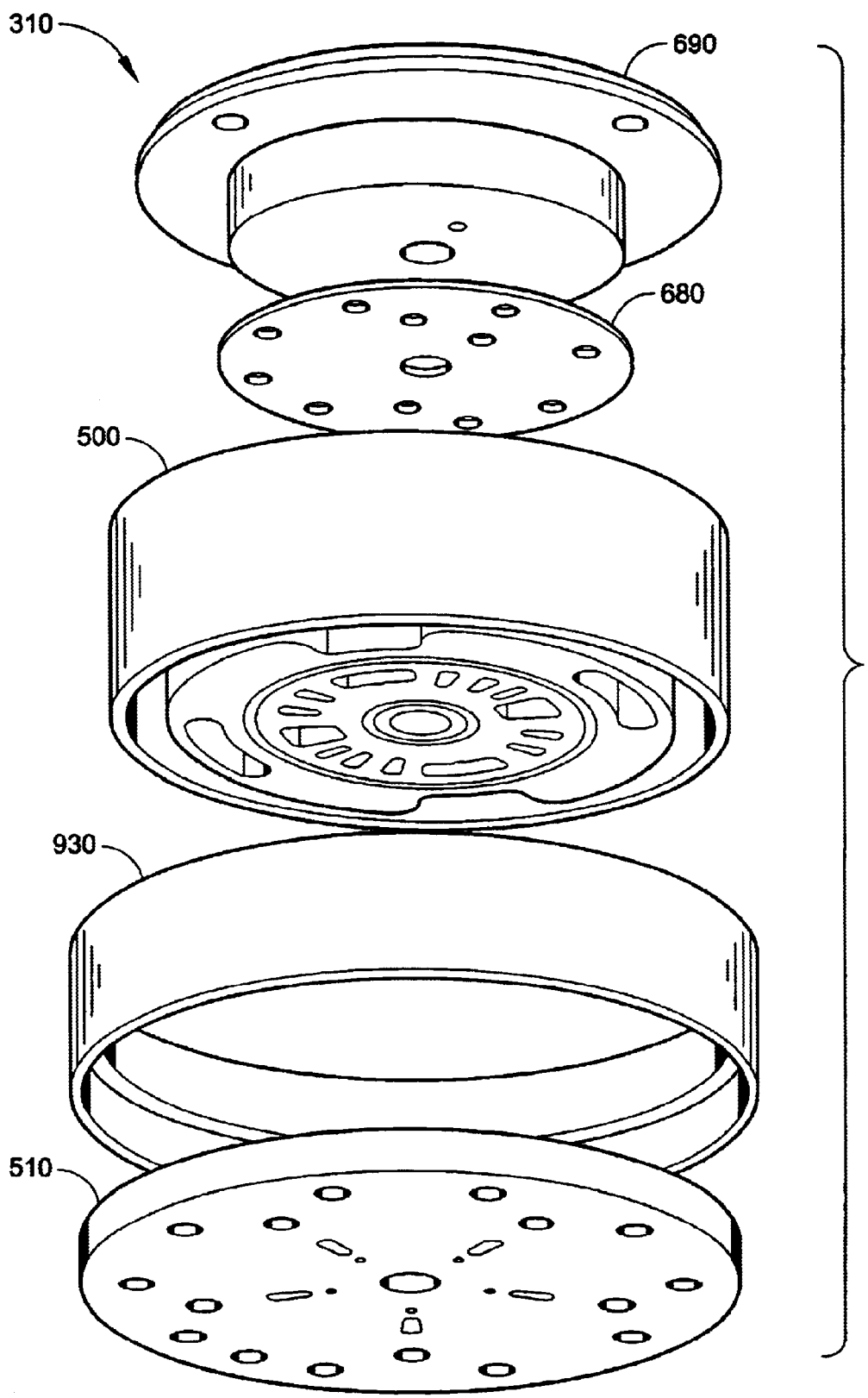
FIGS. 9A and 9B are a bottom perspective, exploded view and a top perspective, exploded view respectively of an embodiment of a rotary valve assembly including a centering ring that may be used with the concentrator illustrated in FIGS. 3A and 3B.
Figure 9B:
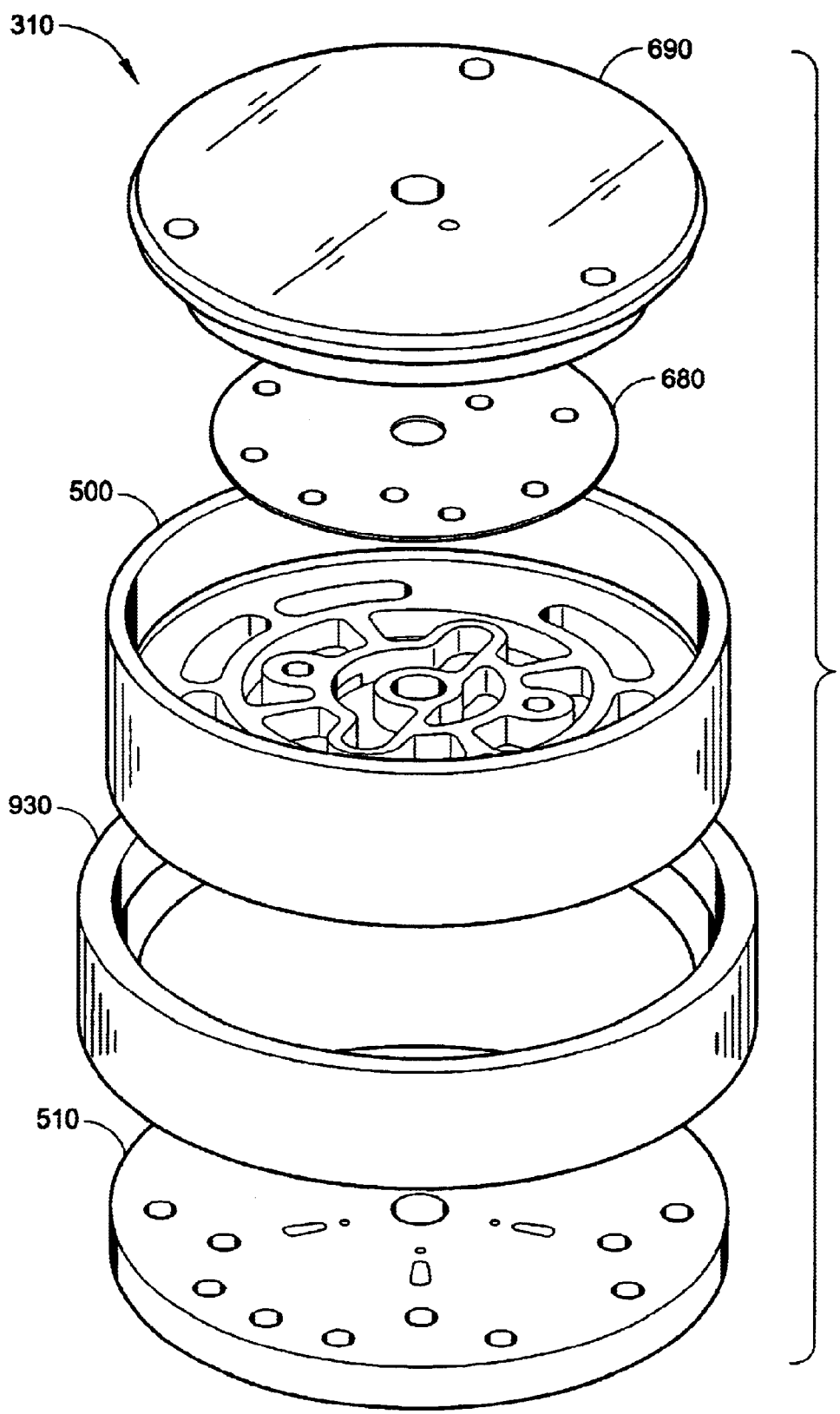

With reference to FIGS. 9A and 9B, a rotary valve assembly constructed in accordance with another embodiment of the invention includes an alternative centering mechanism to maintain the rotating valve shoe 500 in a fixed position relative to the valve port plate 510. A circular centering ring 930 fits snugly over the smooth cylindrical sidewall 530 of the rotary valve shoe 500 and the smooth cylindrical sidewall 710 of the stationary valve port plate 510. The circular ring 930 centers the rotary valve shoe 500 relative to the valve port plate 510 by holding the rotary shoe 500 in a fixed position relative to the port plate 510 while at the same time allowing the rotary valve shoe 500 to rotate.

Figure 10A:
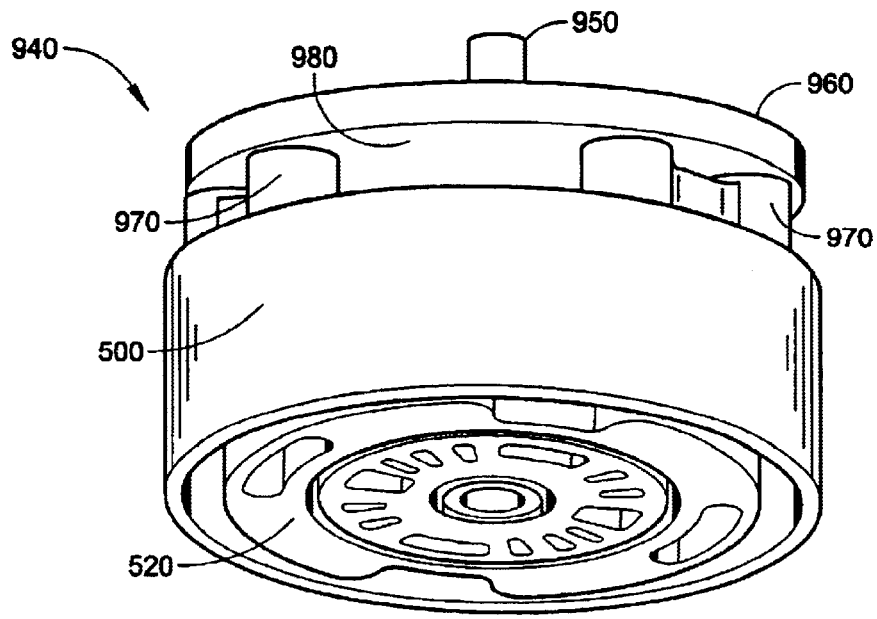
FIG. 10A is a bottom perspective view of an embodiment of a rotary valve shoe, a motor drive, and a pair of elastic chain links that may be used with the concentrator illustrated in FIGS. 3A and 3B.
Figure 10B:
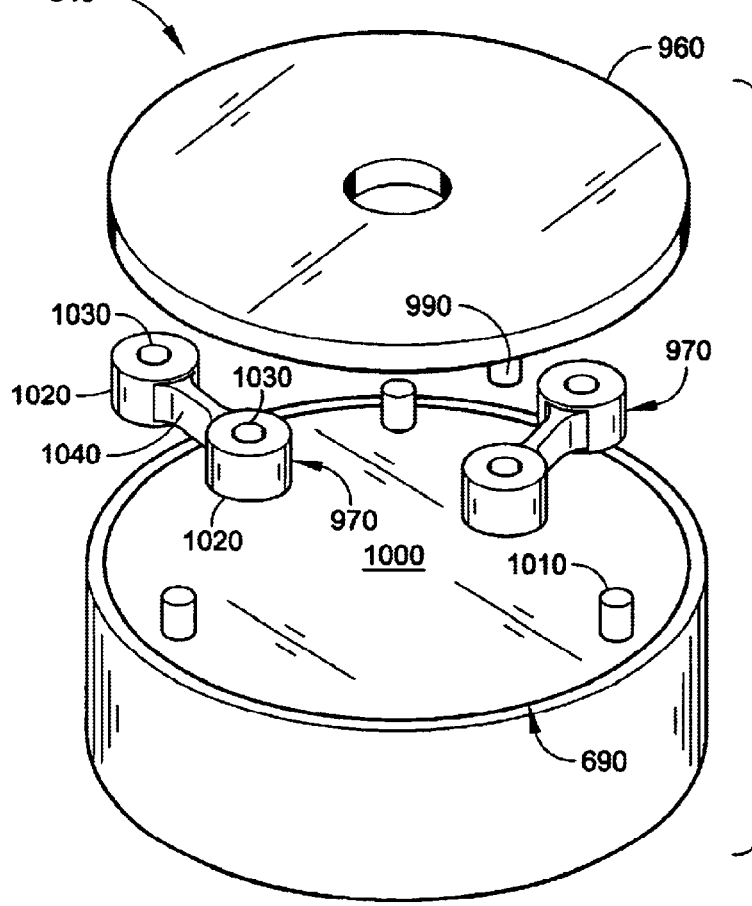
FIGS. 10B and 10C are a top perspective, exploded view and a bottom perspective, exploded view respectively of the rotary valve shoe, motor drive, and pair of elastic chain links illustrated in FIG. 10A.
Figure 10C:
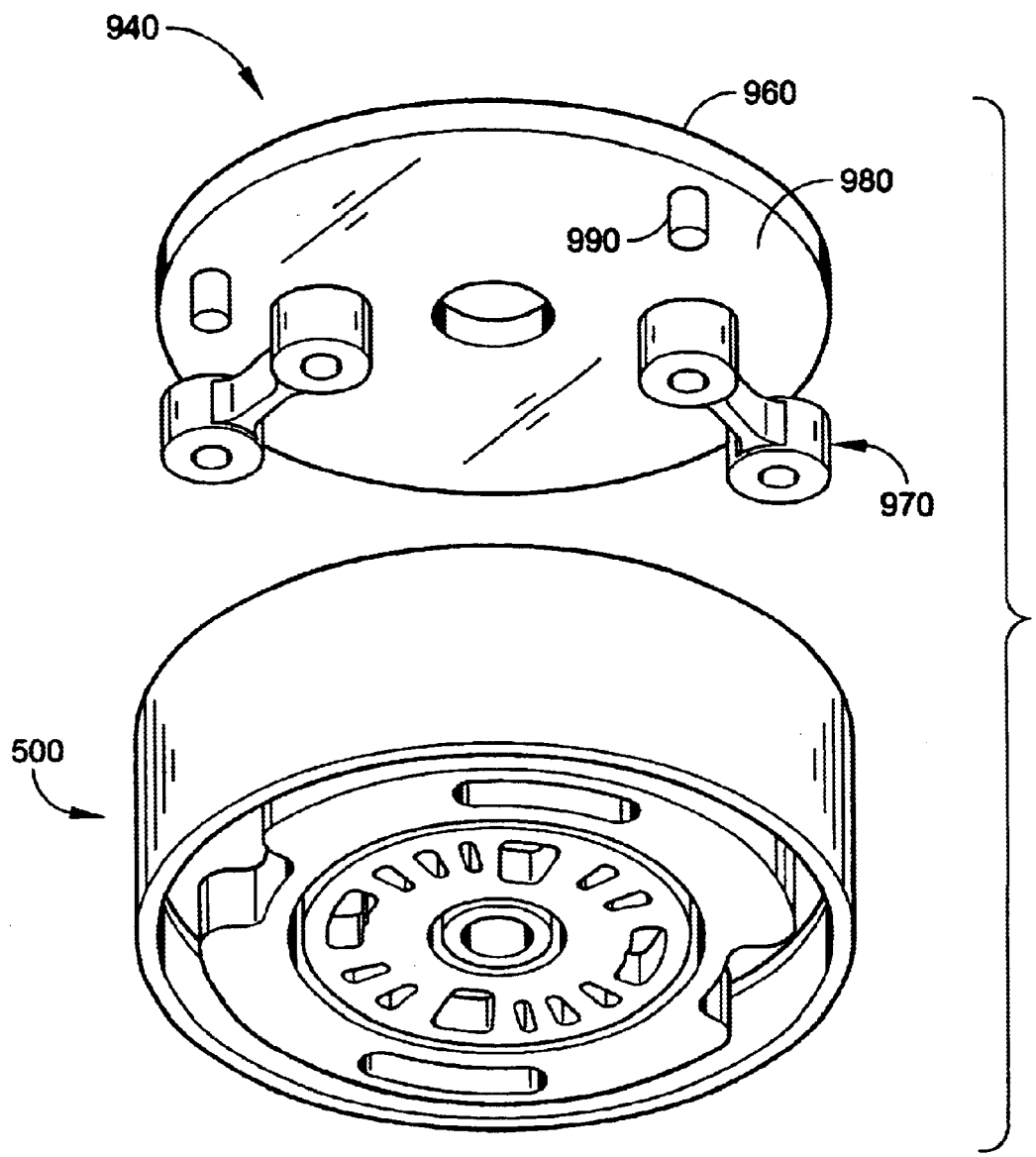

With reference to FIGS. 10A–10C, an embodiment of an elastic link for coupling the motor 118 to the valve shoe 500 will now be described. A drive mechanism 940 includes a drive shaft 950, a drive wheel 960, and three (two shown) elastic chain links 970. The drive shaft 950 may be connected to the motor 118 for rotating the drive wheel 960. With reference to FIG. 10C, a lower side 980 of the drive wheel 960 may include downwardly protruding cylindrical support posts 990. Similarly, with reference to FIG. 10B, an upper side 1000 of the second valve shoe cover 690 may include upwardly protruding cylindrical support posts 1010. The elastic chain links 970 are preferably made of semi-rigid, elastic material (such as silicon rubber) and have a generally wrench-shaped configuration. Each elastic chain link 970 includes cylindrical receiving members 1020 with central cylindrical bores 1030. The cylindrical receiving members 1020 are joined by a narrow connecting member 1040. The drive wheel 960 is coupled to the second valve shoe cover 690 through the elastic chain links 970. One receiving member 1020 of each elastic chain link receives the support post 990 of the drive wheel 960 and the other receiving member 1020 receives the support post 1010 of the second valve shoe cover 690. In the past, rigid connections were made between the motor and the rotating valve shoe. These rigid connections caused the rotating valve shoe to be affected by vibration or other non-rotational movement of the motor. The elastic chain links 970 absorb the vibration and non-rotational movement of the motor, preventing this detrimental energy from being imparted to the rotating valve shoe 500.

FIG. 11 is a table of experimental data from a concentrator similar to the concentrator 114 shown and described above with respect to FIGS. 3–10. As shown by this table, the recovery of oxygen from air with the concentrator 114 is 45–71% at about 90% purity. The ratio of adiabatic power (Watts) to oxygen flow (Liters Per Minute) is in the range of 6.2 W/LPM to 23.0 W/LPM. As defined in Marks' Standard Handbook for Mechanical Engineers, Ninth Edition, by Eugene A. Avallone and Theodore Baumeister, the equation for adiabatic power, tanken from the equation from adiabatic work, is as follows:

$$\text{Power} = \frac{W}{t} = P_1 V_1 \left(\frac{k}{1-k}\right)\left[\left(\frac{P_2}{P_1}\right)^{\frac{k-1}{k}} - 1\right] C$$

Power = Adiabatic Power (Watts)

$W$ = Adiabatic Work (Joule)

$t$ = time (Second)

$P_1$ = Atomspheric Pressure (psia)

$P_2$ = Compressor/Vacuum pressure (psia)

$k$ = Ratio of Specific Heats = constant = 1.4 (for air)

$V_1$ = Volumetric flow rate at atmospheric pressure (SLPM)

$C$ = Conversion Factor, added by authors for clarity = 0.114871 Watts/psi/LPM

B. Energy Source

Figure 12:
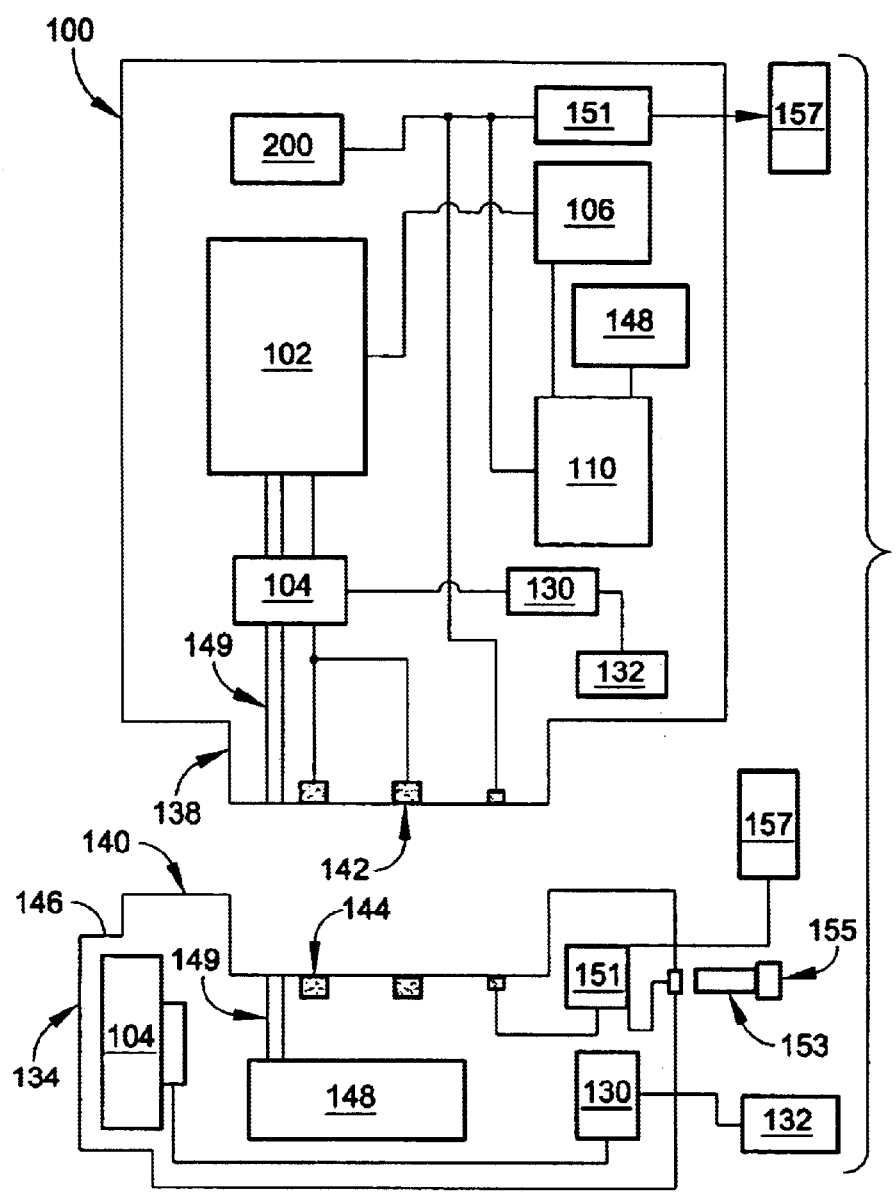
FIG. 12 is a schematic illustration of a further embodiment of the portable oxygen concentration system and an embodiment of a cradle for use with the portable oxygen concentration system.

With reference additionally to FIG. 12, in order to properly function as a lightweight, portable system 100, the system 100 must be energized by a suitable rechargeable energy source. The energy source preferably includes a rechargeable battery 104 of the lithium-ion type. It will be readily apparent to those skilled in the art that'. the system 100 may be powered by a portable energy source other than a lithium-ion battery. For example, a rechargeable or renewable fuel cell may be used. Although the system is generally described as being powered by a rechargeable battery 104, the system 100 may be powered by multiple batteries. Thus, as used herein, the word "battery" includes one or more batteries. Further, the rechargeable battery 104 may be comprised of one or more internal and/or external batteries. The battery 104 or a battery module including the battery 104 is preferably removable from the system 100. The system 100 may use a standard internal battery, a low-cost battery, an extended-operation internal battery, and an external secondary battery in a clip-on module.

The system 100 may have a built-in adapter including battery charging circuitry 130 and one or more plugs 132 configured to allow the system 100 to be powered from a DC power source (e.g., car cigarette lighter adapter) and/or an AC power source (e.g., home or office 110 VAC wall socket) while the battery 104 is simultaneously being charged from the DC or AC power source. The adapter or charger could also be separate accessories. For example, the adapter may be a separate cigarette lighter adapter used to power the system 100 and/or charge the battery 104 in an automobile. A separate AC adapter may be used to convert the AC from an outlet to DC for use by the system 100 and/or charging the battery 104. Another example of an adapter may be an adapter used with wheel chair batteries or other carts.

Alternatively, or in addition, a battery-charging cradle 134 adapted to receive and support the system 100 may have an adapter including battery charging circuitry 130 and a plug 132 that also allow the system 100 to be powered while the battery 104 is simultaneously being charged from a DC and/or AC power source.

The system 100 and cradle 134 preferably include corresponding mating sections 138, 140 that allow the system 100 to be easily dropped into and onto the cradle 134 for docking the system 100 with the cradle 134. The mating sections 138,140 may include corresponding electrical contacts 142, 144 for electrically connecting the system 100 to the cradle 134.

The cradle 134 may be used to recharge and/or power the system 100 in the home, office, automobile, etc. The cradle 134 may be considered part of the system 100 or as a separate accessory for the system 100. The cradle 134 may include one or more additional charging receptacles 146 coupled to the charging circuitry 130 for charging spare battery packs 104. With a charging receptacle 146 and one or more additional battery packs 104, the user can always have a supply of additional fresh, charged batteries 104.

In alternative embodiments, the cradle 134 may come in one or more different sizes to accommodate one or more different types of systems 100.

The cradle 134 and/or system 100 may also include a humidifying mechanism 148 for adding moisture to the air flow in the system 100 through appropriate connections 149. In an alternative embodiment of the invention, the humidifying mechanism 148 may be separate from the system 100 and the cradle 134. If separate from the system 100 and cradle 134, the cradle 134 and/or system 100 may include appropriate communication ports for communicating with the separate humidifying mechanism 148. The cradle 134 may also include a receptacle adapted to receive a separate humidifying mechanism 148 for use with the system 100 when the system 100 is docked at the cradle 134.

The cradle 134 and/or system 100 may also include a telemetry mechanism or modem 151 such as a telephone modem, high-speed cable modem, RF wireless modem or the like for communicating the control unit 110 of the system 100 with one or more remote computers. To this end, the cradle 135 may include a line 153 with a cable adapter or telephone jack plug 155, or a RF antenna 157. In an alternative embodiment of the invention, the telemetry mechanism or modem 151 may be separate from the cradle 134 and to this end, the cradle 134 or system 100 may include one or more appropriate communication ports, e.g., a PC port, for directly communicating the telemetry mechanism or modem 151 with the cradle 134 or system 100. For example, the cradle 134 may be adapted to communicate with a computer (at the location of the cradle) that includes the telemetry mechanism or modem 151. The computer may include appropriate software for communicating information described below using the telemetry mechanism or modem 151 with the one or more remote computers.

The telemetry mechanism or modem 151 may be used to communicate physiological information of the user such as, but not by way of limitation, heart rate, oxygen saturation, respiratory rate, blood pressure, EKG, body temperature, inspiratory/expiratory time ratio (I to E ratio) with one or more remote computers. The telemetry mechanism or modem 151 may be used to communicate other types of information such as, but not by way of limitation, oxygen usage, maintenance schedules on the system 100, and battery usage with one or more remote computers.

A user ideally uses the system 100 in its cradle 134 at home, at the office, in the automobile, etc. A user may decide to have more than one cradle, e.g., one at home, one at the office, one in the automobile, or multiple cradles at home, one in each room of choice. For example, if the user has multiple cradles 134 at home, when the user goes from room to room, e.g., from the family room to the bedroom, the user simply lifts the system 100 out of its cradle 134 in one room, and walks to the other room under battery operation. Dropping the system 100 in a different cradle 134 in th destination room restores the electrical connection between the system 100 and the AC power source. Since the system's batteries 104 are constantly charging or charged when located in the cradle 134, excursions outside the home, office, etc. are as simple as going from room to room in the user's home.

Because the system 100 is small and light (2–15 pounds), the system 100 may simply be lifted from the cradle 134 and readily carried, e.g., with a shoulder strap, by an average user to the destination. If the user is unable to carry the system 100, the system 100 may be readily transported to the destination using a cart or other transporting apparatus. For an extended time away from home, office, etc., the user may bring one or more cradles 134 for use at the destination. Alternatively, in the embodiment of the system 100 including the built-in adapter, power may be drawn from power sources such as a car cigarette lighter adapter and/or an AC power outlet available at the destination. Further, spare battery Packs 104 may be used for extended periods away from standard power sources.

If the battery pack 104 includes multiple batteries, the system 100 may include a battery sequencing mechanism to conserve battery life as is well known in the cellphone and laptop computer arts.

C. Output Sensor

Figure 13:
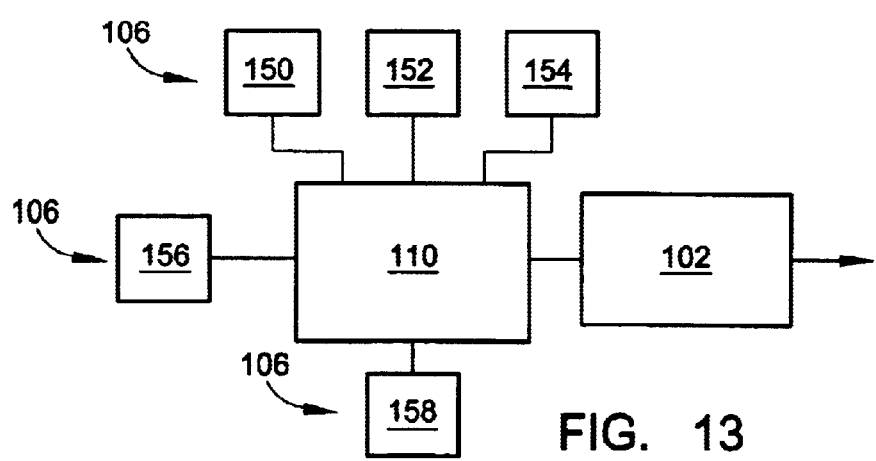
FIG. 13 is a block diagram of the one or more sensors that may be used with an embodiment of the portable oxygen concentration system.

With reference to FIGS. 1, 2 and 13, one or more output sensors 106 are used to sense one or more conditions of the user 108, environment, etc. to determine the oxygen flow rate needs of the user and, hence, the oxygen flow rate output requirements for the system 100. A control unit 110 is linked to the one or more output sensors 106 and the oxygen gas generator 102 to control the oxygen generator 102 in response to the condition(s) sensed by the one or more output sensors 106. For example, but not by way of limitation, the output sensor(s) 106 may include any or all of the activity sensors shown and described in U.S. Pat. No. 5,928,189, which is incorporated by reference as though set forth in full. These output sensors include a pressure sensor 150, a position sensor 152, an acceleration sensor 154, as well as a physiological condition or metabolic sensor 156 and an altitude sensor 158.

The first three sensors 150, 152, 154 (and, in certain circumstances, the physiological condition sensor 156) are activity sensors because these sensors provide a signal representing activity of the user 108. In the delivery of oxygen with a portable oxygen concentration system, it is important to deliver an amount of oxygen gas proportional to the activity level of the user 108 without delivering too much oxygen. Too much oxygen may be harmful for the user 108 and reduces the life of the battery 104. The control unit 110 regulates the oxygen gas generator 102 to control the flow rate of oxygen gas to the user 108 based on the oneor more signals representative of the activity level of the user produced by the one or more sensors 106. For example, if the output sensor(s) 106 indicates that the user 108 has gone from an inactive state to an active state, the control unit 110 may cause the oxygen gas generator 102 to increase the flow rate of oxygen gas to the user 108 and/or may provide a burst of oxygen gas to the user 108 from a high-pressure oxygen reservoir to be described. If the output sensor(s) 106 indicates that the user 108 has gone from an active state to an inactive state, the control unit 110 may cause the oxygen gas generator 102 to reduce the flow rate of oxygen gas to the user.

In an embodiment of the invention, the amount of oxygen gas supplied is controlled by controlling the speed of the compressor motor 118 via the variable-speed controller 119.

Alternatively, or in addition to the variable-speed controller, the supply of oxygen gas may be controlled by the supply valve 160 located in the supply line 121 between the oxygen gas (generator 102 and the user 108. For example, the supply valve 160 may be movable between at least a first position and a second position, the second position allowing a greater flow of concentrated gaseous oxygen through than the first position. The control unit 110 may cause the supply valve 160 to move from the first position to the second position when one or more of the activity level sensors 152, 154,156 senses an active level of activity of the user 108. For example, the control unit 110 may include a timer, and when an active level is sensed for a time period exceeding a predetermined timed period, the control unit 110 causes the valve 160 to move from the first position to the second position.

Examples of pressure sensors 150 include, without limitation, a foot switch that indicates when a user is in a standing position compared to a sedentary position, and a seat switch that indicates when a user is in a seated position compared to a standing position.

A pendulum switch is an example of a position sensor 152. For example, a pendulum switch may include a thigh switch positioned pendulously to indicate one mode when the user is standing, i.e., the switch hangs vertically, and another mode when the user seated, i.e., the thigh switch raised to a more horizontal position. A mercury switch may be used as a position sensor.

An acceleration sensor 158 such as an accelerometer is another example of an activity sensor that provides a signal representing activity of the user.

The physiological condition or metabolic sensor 156 may also function as an activity sensor. The physiological condition sensor 156 may be used to monitor one or more physiological conditions of the user for controlling the oxygen gas generator 102 or for other purposes. Examples of physiological conditions that may be monitored with the sensor 156 include, but without limitation, blood oxygen level, heart rate, respiration rate, blood pressure, EKG, body temperature, and I to E ratio. An oximeter is an example of a sensor that is preferably used in the system 100. The oximeter measures the blood oxygen level of the user, upon which oxygen production may be at least partially based.

An altitude sensor 158 is an example of an environmental or ambient condition sensor that may sense an environmental or ambient condition upon which control of the supply of oxygen gas to the user may be at least partially based. The altitude sensor 158 may be used alone or in conjunction with any or all of the above sensors, the control unit 110 and the oxygen gas generator 102 to control the supply of oxygen gas to the user in accordance with the sensed altitude or elevation. For example, at higher sensed elevations, where air is less concentrated, the control unit may increase the flow rate of oxygen gas to the user 108 and at lower sensed elevations, where air is more concentrated, the control unit may decrease the flow rate of oxygen gas to the user 108 or maintain it at a control level.

It will be readily apparent to those skilled in the art that one or more additional or different sensors may be used to sense a condition upon which control of the supply of oxygen gas to the user may be at least partially based. Further, any or all of the embodiments described above for regulating the amount of oxygen gas supplied to the user 108, i.e., variable-speed controller 119, supply valve 160, (or alternative embodiments) may be used with the one or more sensors and the control unit 110 to control of the supply of oxygen gas to the user 108.

D. Control Unit

Figure 14:
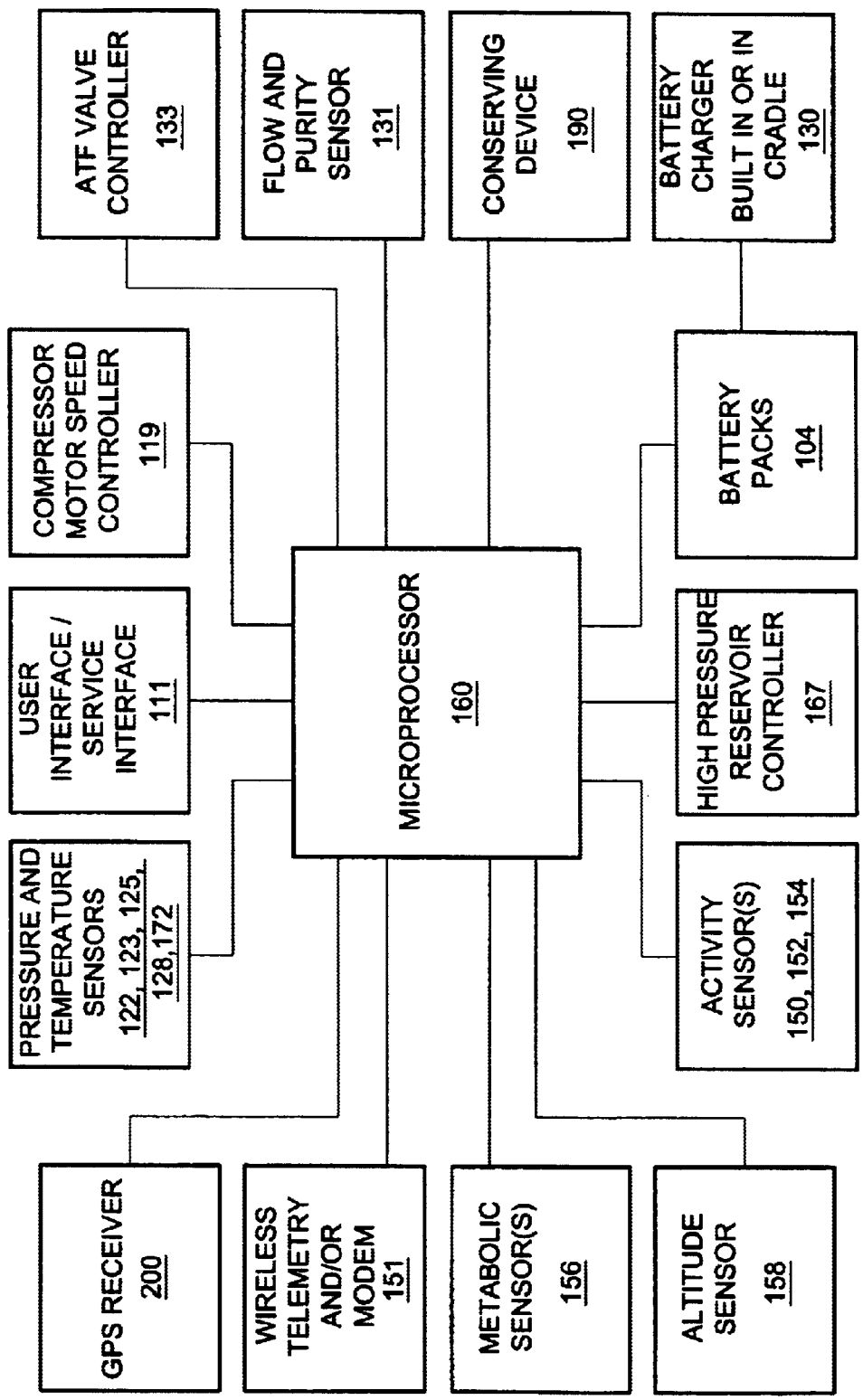
FIG. 14 is a block diagram of the one or more components that may be controlled by the control unit of the portable oxygen concentration system.

With reference to FIG. 14, the control unit 110 may take any well-known form in the art and includes a central microprocessor or CPU 160 in communication with the components of the system described herein via one or more interfaces, controllers, or other electrical circuit elements for controlling and managing the system. The system 100 may include a user interface (FIG. 14) as part of the control unit 110 or coupled to the control unit 110 for allowing the user, provider, doctor, etc. to enter information, e.g., prescription oxygen level, flow rate, activity level, etc., to control the system 100.

The main elements of an embodiment of the system 100 have been described above. The following sections describe a number of additional features, one or more of which may be incorporated into the embodiments of the invention described above as one or more separate embodiments of the invention.

II. Conserving Device

With reference to FIG. 15, a conserving device or demand device 190 may be incorporated into the system 100 to more efficiently utilize the oxygen produced by the oxygen gas generator 102. During normal respiration, a user 108 inhales for about one-third of the time of the inhale/exhale cycle and exhales the other two-thirds of the time. Any oxygen flow provided to the user 108 during exhalation is of no use to the user 108 and, consequently, the additional battery power used to effectively provide this extra oxygen flow is wasted. A conserving device 190 may include a sensor that senses the inhale/exhale cycle by sensing pressure changes in the cannula 111 or another part of the system 100, and supply oxygen only during the inhale portion or a fraction of the inhale portion of the breathing cycle. For example, because the last bit of air inhaled is of no particular use because it is trapped between the nose and the top of the lungs, the conserving device 190 may be configured to stop oxygen flow prior to the end of inhalation, improving the efficiency of the system 100. Improved efficiency translates into a reduction in the 20 size, weight, cost and power requirements of the system 100.

The conserving device 190 may be a stand-alone device in the output line of the system 100, similar to a regulator for scuba diving, or may be coupled to the control unit 110 for controlling the oxygen generator 102 to supply oxygen only during inhalation by the user 108.

The conserving device 190 may include one or more of the sensors described above. For example, the conserving device may include a sensor for monitoring the respiration rate of the user.

The system 100 may also include a special cannula retraction device for retracting the cannula ill when not in use. Further, the cannula 111 may come in different lengths and sizes.

III. High-Pressure Reservoir

With reference to FIG. 16, a high-pressure reservoir 164 may be located in a secondary line 166 for delivering an additional supply of oxygen gas to the user 108 when the oxygen gas generator 102 can not meet the oxygen gas demands of the user 108. Any of the components described below in the secondary line 166 may be coupled to the control unit 110 or a high-pressure reservoir controller 167 (FIG. 14) for control thereby. Exemplary situations where this additional oxygen gas need may occur are when a user suddenly goes from an inactive state to an active state, e.g., when getting out of a chair, when the system 100 is turned on, or when the system 100 goes from a conserving mode or sleep mode to an active mode. As used herein, secondary line 166 refers to the tubing, connectors, etc. used to connect the components in the line. A valve 168 may be controlled by the control unit 110 to allow gaseous oxygen to flow into the secondary line 166. The valve 168 may be configured to allow simultaneous flow to both the supply line 121 and the secondary line 166, flow to only the supply line 121, or flow to only the secondary line 166.

A pump or compressor 168, which is preferably powered by the motor 118, delivers the oxygen gas at a relatively high pressure, e.g., at least approximately 100 psi, to the high-pressure reservoir 164.

An oxygen-producing electrochemical cell 171 may be used in conjunction with or instead of the elements described in the secondary line 166 to supply additional oxygen gas to the user 108. U.S. Pat. No. 6,010,317 to Maget, et al., which is incorporated by reference as though set forth in full, describes an electrochemical cell that may be used for this purpose. For example the electrochemical cell 171 may be used to deliver oxygen gas at a relatively high pressure to the highpressure reservoir 164.

A pressure sensor 172 is in communication with the high-pressure reservoir 164 and the control unit 110 so that when the pressure in the high-pressure reservoir 164 reaches a certain limit, the control unit 110 causes the valve 168 to direct oxygen to the secondary line 166.

A regulator 174 may be used to control flow and reduce pressure of the oxygen gas to the user 108.

A valve 176 may also be controlled by the control unit 110 to allow gaseous oxygen from the high-pressure reservoir 164 to flow into the supply line 121 when the user 108 requires an amount of oxygen gas that cannot be met by the oxygen gas generator 102. The valve 176 may be configured to allow simultaneous flow from the oxygen gas generator 102 and the high-pressure reservoir 164, from only the oxygen gas generator 102, or from only the high-pressure reservoir 164.

The one or more sensors 106 are interrelated with the control unit 110 and the oxygen gas generator 102 so as to supply an amount of oxygen gas equivalent to the oxygen gas needs of the user 108 based at least in part upon one or more conditions sensed by the one or more sensors 106. When the oxygen gas generator 102 cannot meet the oxygen gas demands of the user 108, the control unit 110, based at least in part upon sensing one or more conditions indicative of the oxygen needs of the user, may cause the high-pressure reservoir 164 (via the valve 176) to supply the additional oxygen gas needed.

In the scenario where the oxygen gas generator 102 is capable of supplying the full oxygen gas needs of the user 108, but is simply turned off or is in a conserving or sleep mode, the period of time that the high-pressure reservoir 164 supplies the oxygen gas, i.e., the period of time that the valve 176 connects the high-pressure reservoir 164 with the supply line 121, is at least as long as the time required for the oxygen gas generator 102 to go from an off or inactive condition to an on or active condition. In another scenario, the control unit 110 may cause oxygen gas to be supplied to the user from the high-pressure reservoir 164 when the demand for gaseous oxygen by the user exceeds the maximum oxygen gas output of the oxygen gas generator 102. Although the high-pressure reservoir 164 is shown and described as being filled by the oxygen gas generator 102, in an alternative embodiment, the high-pressure reservoir 164 may be filled by a source outside or external to the system.

IV. Global Positioning System

With reference back to FIG. 12, in an alternative embodiment of the invention, the system 100 may include a global positioning system (GPS) receiver 200 for determining the location of the system 100. The location of the receiver 200 and, hence, the user 108 can be transmitted to a remote computer via the telemetry mechanism or modem 151. This may be desirable for locating the user 108 in the event the user has a health problem, e.g., heart attack, hits a panic button on the system, an alarm is actuated on the system, or for some other reason.

V. Additional Options and Accessories

In addition to the cradle 134, the portable oxygen concentration system 100 may include additional options and accessories. A number of different types of bags and carrying cases such as, but not by way of limitation, a shoulder bag, a backpack, a fanny pack, a front pack, and a split pack in different colors and patterns may be used to transport the system 100 or other system accessories. A cover may be used to shield the system from inclement weather or other environmental damage. The system 100 may also be transported with a rolling trolley/cart, a suit case, or a travel case. The travel case may be designed to carry the system 100 and include enough room to carry the cannulae 111, extra batteries, an adapter, etc. Examples of hooks, straps, holders for holding the system 100 include, but not by way of limitation, hooks for seatbelts in cars, hooks/straps for walkers, hooks/straps, for wheel chairs, hooks/straps for hospital beds, hooks for other medical devices such as ventilators, hooks/straps for a golf bag or golf cart, hooks/straps for a bicycle, and a hanging hook. The system 100 may also include one or more alarm options. An alarm of the system 100 may be actuated if, for example, a sensed physiological condition of the user 108 falls outside a pre-defined range. Further, the alarm may include a panic alarm that may be manually actuated by the user 108. The alarm may actuate a buzzer or other sounding device on the system 100 and/or cause a communication to be sent via the telemetry mechanism or modem 151 to another entity, e.g., a doctor, a 911 dispatcher, a caregiver, a family member, etc.

Although this invention has been described in terms of certain preferred embodiments, other embodiments apparent to those of ordinary skill in the art are also within the scope of this invention. Accordingly, the scope of this invention is intended to be defined only by the claims that follow.

We claim:

1. A portable oxygen concentrator system adapted to be readily transported by a user, comprising:
   a rechargeable energy source;
   a concentrator powered by said energy source and adapted to convert ambient air into concentrated oxygen gas for said user, the concentrator including a plurality of adsorption beds and a rotary valve assembly, the rotary valve assembly relatively rotatable with respect to the plurality of adsorption beds to provide valving action for selectively transferring fluids through the plurality of adsorption beds for converting ambient air into concentrated oxygen gas for said user,
   wherein the ratio of adiabatic power to oxygen flow for the concentrator is in the range of 6.2 W/LPM to 23.0 W/LPM.

2. The portable oxygen concentrator system of claim 1, wherein the concentrator includes exactly five adsorption beds.

3. The portable oxygen concentrator system of claim 1, wherein the rotary valve assembly includes a valve port plate and a rotary valve shoe having respective engaged surfaces and relatively rotatable about a common center of rotation to provide valving action for selectively transferring fluids therethrough, and a centering mechanism other than a motor to center the rotary valve shoe relative to the valve port plate.

4. The portable oxygen concentrator system of claim 3, wherein the valve port plate and the rotary valve shoe include respective central holes, and the centering mechanism includes a centering pin disposed in the central holes of the valve port plate and rotary valve shoe to center the rotary valve shoe relative to the valve port plate.

5. The portable oxygen concentrator system of claim 3, wherein the valve port plate and rotary valve shoe include cylindrical sidewalls, and the centering mechanism includes a centering ring disposed around the sidewalls of the valve port plate and the rotary valve shoe to center the rotary valve shoe relative to the valve port plate.

6. The portable oxygen concentrator system of claim 1, wherein the adsorption beds carry adsorbent material, and include a first end, a second end, an adsorbent media disposed in the adsorption beds between the first end and the second end, a media retention cap disposed between the adsorbent media and the second end, a spring to urge the media retention cap against the adsorbent material to hold the adsorbent media in place, and the spring not located in a flow path of the adsorption beds.

7. The portable oxygen concentrator system of claim 6, wherein the media retention cap includes a surface that contacts the adsorbent media, the surface including a central hole and a plurality of ribs radiating from the central hole.

8. The portable oxygen concentrator system of claim 6, wherein the media retention cap includes a bottom base with an interior, and the spring is disposed in the interior of the bottom base.

9. The portable oxygen concentrator system of claim 1, wherein the rotary valve assembly includes a valve port plate and a rotary valve shoe having respective engaged surfaces and relatively rotatable about a common center of rotation to provide valving action for selectively transferring fluids therethrough, and the portable oxygen concentrator system further includes a motor to rotate the rotary valve shoe, and one or more elastic links to couple the motor to the rotary valve shoe.

10. The portable oxygen concentrator system of claim 9, wherein the motor includes a drive shaft and a drive wheel with one or more protruding support members, the rotary valve shoe includes one or more protruding support members, and the elastic link connects the one or more protruding support members of the drive wheel with the one or more protruding support members of the rotary valve shoe.

11. The portable oxygen concentrator system of claim 1, wherein the concentrator includes plastic adsorption beds and a metal cover surrounding the plastic adsorption beds.

12. The portable oxygen concentrator system of claim 11, wherein the adsorption beds are, elongated, molded, plastic vessels.

13. The portable oxygen concentrator system of claim 12, wherein the metal cover is made of aluminum and surrounds the adsorption beds to form a product tank.

14. The portable oxygen concentrator system of claim 1, wherein the rotary valve assembly includes a valve port plate and a rotary valve shoe having respective engaged surfaces and relatively rotatable about a common center of rotation to provide valving action to put the adsorption beds in a pressure swing adsorption cycle, and the pressure swing adsorption cyle includes a number of equalization steps in each adsorption bed ranging from two to eight.

15. The portable oxygen concentrator system of claim 14, wherein the pressure swing adsorption cyle includes a number of equalization steps in each adsorption bed ranging from two to six.

16. The portable oxygen concentrator system of claim 14, wherein the pressure swing adsorption cyle includes four equalization steps in each adsorption bed.

17. The portable oxygen concentrator system of claim 14, wherein the equalization steps include a first equalization down step, a second equalization down step, a first equalization up step, and a second equalization up step.

18. The portable oxygen concentrator system of claim 14, wherein adsorption beds include a feed end and a product end, and equalization occurs between product ends of adsorption beds.

19. The portable oxygen concentrator system of claim 1, further including a variable-speed compressor to supply ambient air to the concentrator.

20. The portable oxygen concentrator system of claim 1, wherein recovery of oxygen from air from the concentrator is 45–71% at about 90% purity.

21. The portable oxygen concentrator system of claim 1, wherein the rotary valve assembly includes a valve port plate and a rotary valve shoe having respective engaged surfaces and relatively rotatable about a common center of rotation to provide valving action for selectively transferring fluids therethrough, said valve port plate having at least two ports interconnected with at least two adsorption beds, and said rotary valve shoe having a second valve surface opposite said engaged surface with at least one equalization passage to register with said at least two ports of the port plate to equalize pressure in said at least two adsorption beds.

22. The portable oxygen concentrator system of claim 1, wherein a pressure drop through the rotary valve assembly is no more than 1 PSI when the concentrator is producing 3 LPM of oxygen gas.

23. The portable oxygen concentrator system of claim 1, wherein the rotary valve assembly includes a valve port plate and a rotary valve shoe having respective engaged surfaces and relatively rotatable about a common center of rotation to provide valving action for selectively transferring fluids therethrough, the rotation speed of the rotary valve shoe with respect to the valve port plate is varied in order to provide desired cycle timing for a given production of product.

24. The portable oxygen concentrator system of claim 23, further including a variable-speed compressor to supply compressed ambient air to the concentrator, and the rotation speed of the rotary valve shoe with respect to the valve port plate is varied in combination with variation in the speed of the variable-speed compressor in order to provide desired cycle timing and desired supply rate of ambient air to the concentrator for a given production of product.

25. The portable oxygen concentrator system of claim 1, wherein the rotary valve assembly includes a valve port plate and a rotary valve shoe having respective engaged surfaces and relatively rotatable about a common center of rotation to provide valving action for selectively transferring fluids therethrough, and the rotary valve shoe includes a vacuum sealing mechanism that counteracts a pressure force working to unseat the rotary valve shoe from the valve port plate.

26. A portable oxygen concentrator system adapted to be readily transported by a user, comprising;
    an internal rechargeable energy source;
    an air separation device powered by said energy source and adapted to convert ambient air into concentrated oxygen gas for said user, the air separation device including a plurality of adsorber columns and a rotating valve, the rotating valve relatively rotatable with respect to the plurality of adsorber columns to provide valving action for selectively transferring fluids through the plurality of adsorber columns for converting ambient air into concentrated oxygen gas for said user,
    wherein the portable oxygen concentrator system weighs 2–15 pounds and the adsorber columns each including a layered adsorbent bed having two or more distinct adsorbent material layers.

27. The portable oxygen concentrator system of claim 26, wherein the adsorber columns each include a feed end and a product end, and the two or more distinct adsorbent material layers include at least a water adsorption layer and a nitrogen adsorption layer, the water adsorption layer located closer to the feed end than the nitrogen adsorption layer.

28. The portable oxygen concentrator system of claim 27, wherein the water adsorption layer is an activated alumina.

29. The portable oxygen concentrator system of claim 27, wherein the water adsorption layer is a silica gel.

30. The portable oxygen concentrator system of claim 27, wherein the nitrogen adsorption layer is a lithium exchanged X-type zeolite.

31. A portable oxygen concentrator system adapted to be readily transported by a user, comprising:
    an internal rechargeable energy source;
    an air separation device powered by said energy source and adapted to convert ambient air into concentrated oxygen gas for said user, the air separation device including a plurality of adsorber columns each including a feed end and a product end and at least one valve operable with respect to the plurality of adsorber columns to provide valving action for selectively transferring fluids through the plurality of adsorber columns for convening ambient air into concentrated oxygen gas for said user,
    wherein the portable oxygen concentrator system weighs 2–15 pounds and tie adsorber columns each including a layered adsorbent bed having two or more distinct adsorbent material layers, the two or more distinct adsorbent material layers including at least a water adsorption layer and a nitrogen adsorption layer, the water adsorption layer located closer to the feed end than the nitrogen adsorption layer.

32. The portable oxygen concentrator system of claim 31, wherein the water adsorption layer is an activated alumina.

33. The portable oxygen concentrator system of claim 31, wherein the water adsorption layer is a silica gel.

34. The portable oxygen concentrator system of claim 31, wherein the nitrogen adsorption layer is a lithium exchanged X-type zeolite.

* * * * *